(12) United States Patent
Buddharaju

(10) Patent No.: US 10,441,737 B2
(45) Date of Patent: Oct. 15, 2019

(54) STRAPLESS NASAL INTERFACE DEVICE

(71) Applicant: Venkata Buddharaju, Park Ridge, IL (US)

(72) Inventor: Venkata Buddharaju, Park Ridge, IL (US)

(*) Notice: Subject to any disclaimer, the term of this patent is extended or adjusted under 35 U.S.C. 154(b) by 0 days.

(21) Appl. No.: 15/905,503

(22) Filed: Feb. 26, 2018

(65) Prior Publication Data

US 2018/0177966 A1 Jun. 28, 2018

Related U.S. Application Data

(63) Continuation of application No. 15/810,061, filed on Nov. 11, 2017, which is a continuation-in-part of application No. 15/204,718, filed on Jul. 7, 2016, which is a continuation-in-part of application No. 13/864,853, filed on Apr. 17, 2013, which is a
(Continued)

(51) Int. Cl.
| | |
|---|---|
| *A61M 16/06* | (2006.01) |
| *A61M 16/00* | (2006.01) |
| *A61M 16/08* | (2006.01) |
| *A61J 15/00* | (2006.01) |

(52) U.S. Cl.
CPC ...... *A61M 16/0666* (2013.01); *A61J 15/0053* (2013.01); *A61M 16/0057* (2013.01); *A61M 16/0605* (2014.02); *A61M 16/0616* (2014.02); *A61M 16/0683* (2013.01); *A61M 16/0688* (2014.02); *A61M 16/0875* (2013.01); *A61J 15/0003* (2013.01); *A61M 16/0672* (2014.02); *A61M 2016/0661* (2013.01); *A61M 2205/0238* (2013.01)

(58) Field of Classification Search
CPC .............. A61M 16/06; A61M 16/0605; A61M 16/0616; A61M 16/0666; A61M 16/0672; A61M 16/0683; A61M 16/0688; A61M 2210/0618; A61J 15/0003
See application file for complete search history.

(56) References Cited

U.S. PATENT DOCUMENTS

| | | |
|---|---|---|
| 3,288,136 A | 11/1966 | Lund |
| 4,660,555 A | 4/1987 | Payton |
| | (Continued) | |

OTHER PUBLICATIONS

"Velcro® Brand Adhesivee Options"; retrieved from https://www.velcro.com/business/products/adhesive-options/.*
(Continued)

*Primary Examiner* — Joseph D. Boecker
(74) *Attorney, Agent, or Firm* — Richards Patent Law P.C.

(57) ABSTRACT

A nasal interface device configured to be positioned about a user's nose includes an air supply interface body including an air supply opening, at least one nasal opening, and first and second side slots and first and second elastic members extending through the first and second side slots, respectively, on the air supply interface body. Each of the first and second elastic members includes first and second adhesive means on an outer end thereof distal from the air supply interface body. The nasal interface device includes a bendable metallic member including a bridge portion between first and second ends, wherein the first and second elastic members attach to the first and second ends of the bendable metallic member, respectively.

18 Claims, 23 Drawing Sheets

Related U.S. Application Data continuation of application No. 12/641,094, filed on Dec. 17, 2009, now Pat. No. 8,430,098, said application No. 15/810,061 is a continuation-in-part of application No. 14/930,548, filed on Nov. 2, 2015.

(60) Provisional application No. 61/138,472, filed on Dec. 17, 2008.

(56) References Cited

U.S. PATENT DOCUMENTS

| | | | |
|---|---|---|---|
| 4,782,832 A | 11/1988 | Trimble et al. | |
| 4,932,943 A | 6/1990 | Nowak | |
| 5,535,737 A | 7/1996 | Galbenu | |
| 5,735,272 A * | 4/1998 | Dillon | A61F 5/08 128/207.18 |
| 5,746,201 A | 5/1998 | Kidd | |
| 5,806,525 A | 9/1998 | Pope, Jr. | |
| 6,183,493 B1 | 2/2001 | Zammit | |
| 6,401,716 B1 | 6/2002 | Sword et al. | |
| 6,405,729 B1 | 6/2002 | Thornton | |
| 6,478,026 B1 | 11/2002 | Wood | |
| 6,571,798 B1 | 6/2003 | Thornton | |
| 6,581,594 B1 | 6/2003 | Drew et al. | |
| 6,595,215 B2 | 7/2003 | Wood | |
| 6,669,712 B1 * | 12/2003 | Cardoso | A61M 16/0666 128/200.24 |
| 6,776,162 B2 | 8/2004 | Wood | |
| 6,863,069 B2 | 3/2005 | Wood | |
| 6,994,089 B2 | 2/2006 | Wood | |
| 6,997,187 B2 | 2/2006 | Wood et al. | |
| 7,000,613 B2 | 2/2006 | Wood et al. | |
| 7,156,097 B2 * | 1/2007 | Cardoso | A61M 16/0666 128/206.11 |
| 7,234,465 B2 | 6/2007 | Wood | |
| 7,255,107 B1 * | 8/2007 | Gomez | A61M 16/0666 128/206.11 |
| 8,430,098 B1 * | 4/2013 | Buddharaju | A61M 16/0666 128/204.18 |
| 10,124,139 B2 * | 11/2018 | Matula, Jr. | A61M 16/0666 |
| 2005/0066965 A1 | 3/2005 | Cronk et al. | |
| 2005/0205096 A1 * | 9/2005 | Matula, Jr. | A61M 16/0666 128/207.11 |
| 2005/0252515 A1 | 11/2005 | Wood | |
| 2005/0284479 A1 | 12/2005 | Schrader et al. | |
| 2006/0081252 A1 * | 4/2006 | Wood | A61M 16/0683 128/207.11 |
| 2006/0196509 A1 | 9/2006 | Drew et al. | |
| 2007/0000492 A1 | 1/2007 | Hansel et al. | |
| 2007/0125385 A1 | 6/2007 | Ho et al. | |
| 2007/0125387 A1 | 6/2007 | Zollinger et al. | |
| 2007/0272249 A1 | 11/2007 | Chandran et al. | |
| 2008/0011305 A1 | 1/2008 | Chandran et al. | |
| 2008/0060648 A1 * | 3/2008 | Thornton | A61M 16/06 128/205.25 |
| 2008/0190436 A1 * | 8/2008 | Jaffe | A61M 16/0666 128/207.18 |
| 2008/0264421 A1 | 10/2008 | Kwok et al. | |
| 2008/0276941 A1 * | 11/2008 | Doty | A61M 16/009 128/205.28 |
| 2008/0295846 A1 | 12/2008 | Han et al. | |
| 2008/0302365 A1 | 12/2008 | Cohen et al. | |
| 2009/0107507 A1 | 4/2009 | Moore | |
| 2009/0107508 A1 * | 4/2009 | Brambilla | A61M 16/06 128/207.11 |
| 2009/0139525 A1 | 6/2009 | Schirm | |
| 2009/0183739 A1 | 7/2009 | Wondka | |
| 2009/0308398 A1 | 12/2009 | Ferdinand et al. | |
| 2010/0000534 A1 * | 1/2010 | Kooij | A61M 16/0666 128/204.18 |
| 2010/0018535 A1 | 1/2010 | Chimenti et al. | |
| 2010/0037897 A1 | 2/2010 | Wood | |
| 2010/0229872 A1 * | 9/2010 | Ho | A61M 16/06 128/206.25 |
| 2010/0258128 A1 | 10/2010 | Zollinger et al. | |
| 2011/0011397 A1 | 1/2011 | Ziv et al. | |
| 2011/0067704 A1 * | 3/2011 | Kooij | A61M 16/0666 128/207.18 |
| 2012/0067344 A1 * | 3/2012 | Koschany | A61M 16/06 128/201.22 |
| 2012/0111332 A1 * | 5/2012 | Gusky | A61M 16/0666 128/205.25 |
| 2012/0138060 A1 * | 6/2012 | Barlow | A61M 16/0666 128/205.25 |
| 2012/0216812 A1 * | 8/2012 | Pastoor | A61M 16/0666 128/205.25 |
| 2012/0304999 A1 * | 12/2012 | Swift | A61M 16/06 128/205.25 |
| 2012/0318270 A1 * | 12/2012 | McAuley | A61M 16/06 128/205.25 |
| 2013/0263861 A1 * | 10/2013 | Holtzapple | A61M 16/0666 128/207.18 |
| 2014/0096774 A1 | 4/2014 | Olsen et al. | |
| 2015/0090255 A1 * | 4/2015 | Gulliver | A61M 25/02 128/202.15 |
| 2015/0164726 A1 * | 6/2015 | Ward | A61M 16/0683 128/845 |
| 2015/0359988 A1 * | 12/2015 | Humphries | A61M 16/0666 128/206.24 |
| 2016/0030696 A1 * | 2/2016 | Klenner | A61M 16/0066 128/207.18 |
| 2016/0317773 A1 * | 11/2016 | Buddharaju | A61M 16/0666 |
| 2017/0224942 A1 * | 8/2017 | Barbour | A61M 16/0672 |
| 2017/0281895 A1 * | 10/2017 | Kessler | A61M 16/0688 |
| 2018/0064900 A1 * | 3/2018 | Buddharaju | A61M 16/0616 |

OTHER PUBLICATIONS

Farkas, Leslie; Katic, Marko; Forrest, Christopher, "International Anthropometric Study of Facial Morphology in Various Ethnic Groups/Races", Journal of Craniofacial Surgery: Jul. 2005—vol. 16—Issue 4—p. 615-646, doi: 10.1097/01.scs.0000171847.58031. 9e; retrieved from http://femininebeauty.info/farkas.pdf.*

International Search Report of the International Searching Authority prepared by the USPTO in connection with PCT/US2017/041112, dated Sep. 11, 2017; Entire Document (8 pages).

International Search Report and Written Opinion of the International Searching Authority prepared by the USPTO in connection with PCT/US2018/060237, dated Jan. 28, 2019; Entire Document (10 pages).

Farkas, L et al.; "International Anthropometric Study of Facial Morphology in Various Ethnic Groups/Races", Journal of Craniofacial Surgery: Jul. 2005—vol. 16—Issue 4—p. 615-646; retrieved from http://femininebeauty.info/farkas.pdf; Entire Document (32 pages).

* cited by examiner

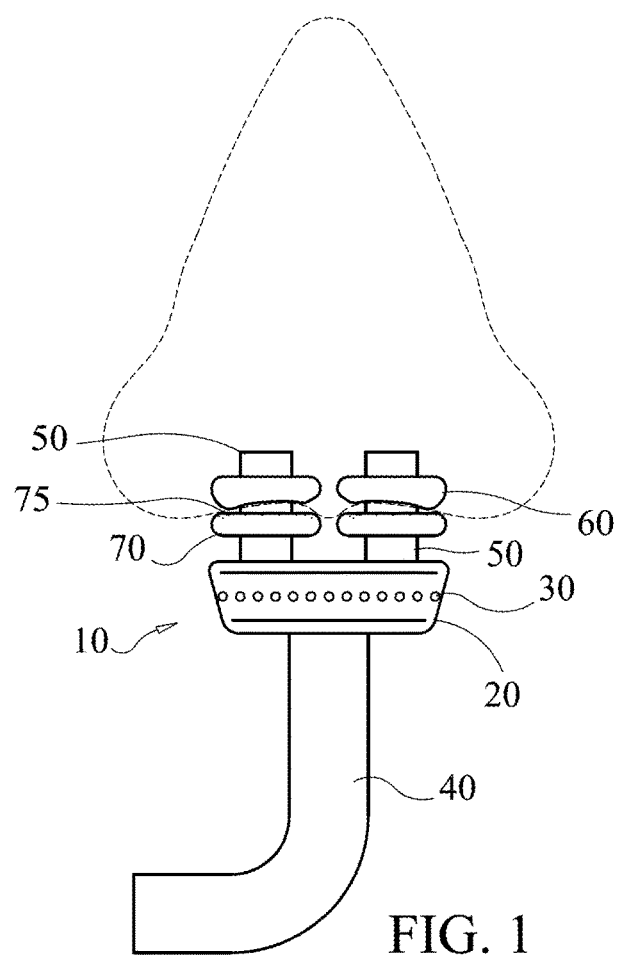
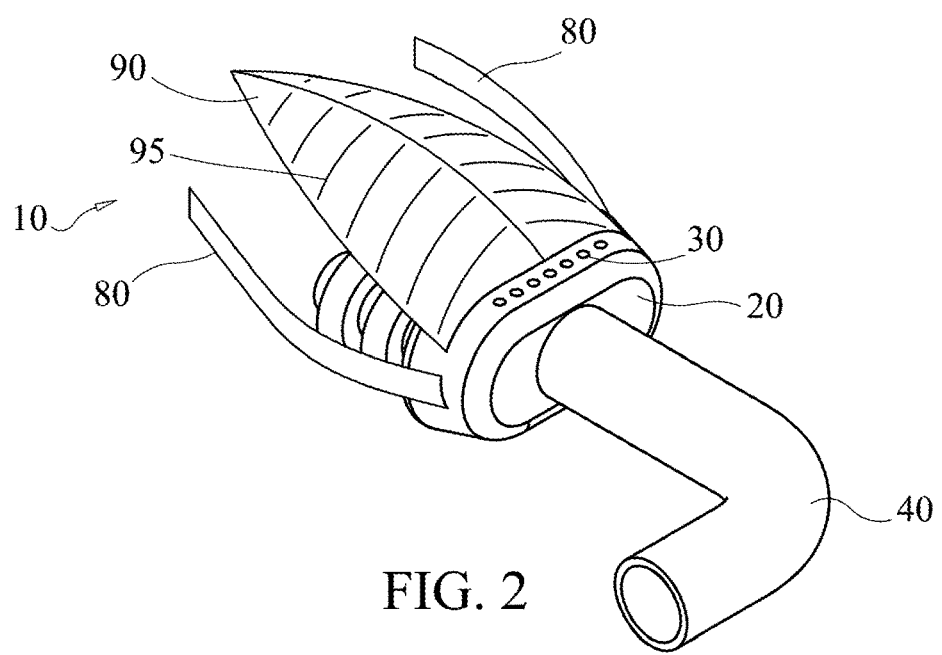

STRAPLESS NASAL INTERFACE DEVICE

CROSS-REFERENCE TO RELATED APPLICATIONS

This application claims the benefit of priority and is a continuation of U.S. application Ser. No. 15/810,061 filed Nov. 11, 2017, which is a continuation-in-part of U.S. application Ser. No. 15/204,718, filed Jul. 7, 2016, which is a continuation-in-part of U.S. application Ser. No. 13/864, 853, filed Apr. 17, 2013, which is a continuation of U.S. application Ser. No. 12/641,094 filed Dec. 17, 2009, which claims the benefit of priority to U.S. Provisional Application No. 61/138,472 filed on Dec. 17, 2008. U.S. application Ser. No. 15/810,061 filed Nov. 11, 2017 is also a continuation-in-part of U.S. application Ser. No. 14/930,548 filed Nov. 2, 2011. The disclosures of each above-mentioned application are incorporated by reference herein.

FIELD OF THE INVENTION

The present invention relates to a straplessnasal interface device, and more particularly, to a device for use with an air supply, a ventilator, a continuous positive airway pressure (CPAP) machine, or a bilevel positive airway pressure (BiPAP) machine for strapless interface with the nasal passages.

BACKGROUND OF THE INVENTION

Nasal passage interface devices are commonly used in conjunction with CPAP devices, BiPAP, ventilators, and other devices. For example, in CPAP applications, a nasal passage interface device is used to provide a passageway for air to enter the nasal passages of the user. Such devices must be secured to the nasal passages so that it remains in place during sleep.

Various existing interfaces are typically held in place by straps or headgear. Such straps can become uncomfortable to the user specifically along the bridge portion of the nose as well as areas of the head in contact with the straps, and can deter use of the device. The user often needs to adjust the straps during the night, and movement of the nasal device often results in leakage. Thus, existing devices are deficient in that they fail to provide an ideal method of attachment.

Numerous such interfaces have been disclosed. For example, U.S. Pat. No. 6,405,729, issued to Thornton, discloses an oral appliance for improving breathing. The appliance includes a mouthpiece and two nasal cushions which sit on the outside of the nose. The device requires the use of the mouthpiece to hold it in place, which would be uncomfortable for a user not in need of the mouthpiece. Without the mouthpiece, the nasal interface would not hold the unit in place.

U.S. Pat. No. 6,478,026, issued to Wood, discloses a nasal ventilation interface. The unit includes tubes which insert into the nose of the user. However, the inserts do not hold the unit in place. The devices require that the air tubes be looped over the ears of the user to hold the unit in place, which would be uncomfortable and easily dislodged during sleep.

Another device is disclosed in U.S. Pat. No. 6,581,594, issued to Drew et al. In this patent, a cumbersome respiratory mask is disclosed which covers the nose of the user. A forehead piece extends from the unit and is attachable to straps to hold the unit in place. The device is rather obtrusive and would have both straps to hold the device in place and a mask, both of which would be uncomfortable for a user.

Yet another device is disclosed in U.S. Pat. No. 7,000,613, issued to Wood et al. In this patent, an interface device also has tubes which extend into the nasal passage. Again, straps in the form of head straps are used to secure the device, which can cause discomfort to a user.

In U.S. Published Patent Application No. 2004/0182397, filed by Wood, a ventilation interface is disclosed having tubes extending into the nares of 5 the nose. In this disclosure, seal portions inserted into the nostrils are disclosed. However, these seal portions are not capable of securing the device to the user, and thus, further securing methods such as straps are needed, again causing potential discomfort to the user.

Another typical interface device is disclosed in U.S. Published Patent Application No. 2007/0272249, filed by Chandran et al. In this device, pillows are included which wedge into the nares of the nose. However, again, these pillows do not secure the device, and straps of various sorts would be required to hold it in place.

U.S. Published Patent Application No. 2010/0000534 by Kooij et al. discloses various nasal interface systems that are secured to the head of the user by connector strips and an adhesive strip. A body of the nasal interface system is positioned about the user's nostrils. The adhesive strip is secured to the bridge of the user's nose and includes Velcro portions on the outer surface that engage with first and second connector strips extending from opposite sides of the body at the user's nostrils. The adhesive strip is a separate component.

In U.S. Pat. No. 5,735,272 issued to Dillon et al., a nasal tube holder for anchoring a nasal tube in a nasal passage is disclosed. The nasal tube holder includes a nasal dilator that is affixed to the bridge of the user's nose. Metallic or plastic truss members on the nasal dilator extend across the bridge of the nose, flexing the nasal dilator into a planar position so as to open up the user's nasal passages.

While a number of other interface devices have been used or disclosed, none of them enable securing via nasal inserts to eliminate the use of straps or air tube contraptions to secure the device to the user's nose. Furthermore, they each pose a level of potential discomfort to the user which render them problematic for sleeping.

Thus, there continues to be a need for a particular suitable nasal passage interface device which can be secured without the need for straps or air tube arrangements, and which provides a greater comfort level to the user.

SUMMARY OF THE DISCLOSURE

The present invention provides, in one aspect, a strapless nasal interface device for use with a CPAP or BIPAP device, or any other ventilator type device. The nasal interface device of the present invention enables the user to secure the device in place without the need for straps or headgear, which can be uncomfortable for the user. Typical PAP devices are secured to the user via straps which wrap around the head of the user. These straps can be very uncomfortable, and can even deter use of the device altogether. Straps can be particularly uncomfortable when the head is tilted in various directions during sleep. This problem may also be particularly present in patients having claustrophobia issues when headgear or straps can be perceived as enclosing on a patient. Children in particular are sensitive to the discomfort of nasal devices and claustrophobic experiences. Additionally, eliminating straps or headgear can make the maintenance and cleaning of the device easier. Providing a light-weight device which can be secured without straps or headgear is thus most advantageous.

In one aspect of the invention, the nasal interface device configured to be positioned about a user's nose, includes an air supply interface connected to an air tube and a bendable element connected to the air supply interface. The bendable element bends to match contours of the user's nose and holds its shape so as to secure a position of the air supply interface relative to the user's nose. The bendable element may be made of a metallic material, such as aluminum. One or more adhesives may be positioned along the band element to promote adherence to the user's face. The adaptability of the bendable element to conform to the shape of the user's nose allows for the bendable element to be used with a variety of shapes and sizes of noses, including the noses of small children as well as adults.

In traditional nasal interface devices, the fulcrum of force that holds the nasal device to the user's face is centered in the back of the head through the use of straps. In the nasal interface devices of the present application, the fulcrum of force is centralized on the bridge of the nose through the use of the bendable element. This repositioning relieves the user of stresses and discomfort related to the straps and minimizes the affected area from the whole head (by means of the straps) to the nasal area (through a nose mask and/or nostril interface tubes).

In one embodiment, the nasal interface device of the present invention includes an interface body which is preferably light weight and low profile. A ventilation tube is connected to the body, such as a tube through which air is supplied via a CPAP or other device. The body may also include exhalation holes. Thus, when the user exhales, the carbon dioxide rich exhalation air can exit through the exhalation holes, allowing new air to enter. In other devices, the nasal interface device may be used to position a cannula that is connected to an oxygen tank so that the nasal prongs of the cannula are at the user's nostrils. In a further embodiment, the nasal interface device may be used to maintain the positioning of a feeding tube at the user's nostrils.

The bendable element may be a flexible strip of material with a first bend corresponding to contours of a bridge area of the user's nose. As used throughout the present application, the bridge, also referred to as the bridge area, includes the bridge of the user's nose and an area adjacent to the bridge, including at least about 2 mm, and preferably about 4 mm, below the bridge of the user's nose. The bendable element may also include first and second side portions between the first bend and first and second ends, respectively, wherein the first and second side portions correspond to contours of sides of the user's nose. The bendable element may also include second and third bends, where the first and second side portions are between the first bend and the second and third bends, respectively. The bendable element may also include fourth and fifth bends adjacent to the first and second ends, respectively.

In yet another aspect, a breathing interface device includes a housing or air supply interface defining a chamber. The housing includes a first nostril tube in fluid communication with the chamber, a second nostril tube in fluid communication with the chamber, and a first opening in fluid communication with the chamber and a positive pressure source. The breathing interface device further includes a facial patch adherable to a portion of a user's face and has a contact surface, and an attachment flap rotatably couplable to the housing and releasably couplable to the facial patch. The bendable element may be secured to an underside of the facial patch. In some embodiments, the facial patch is a nose mask. The bendable element may be positioned along an outer edge of the nose mask.

In some embodiments, the height of the bendable element (the distance between the first bend of the bendable element and the air supply interface) may be adjusted to accommodate for various sizes and shapes of users' noses, from pediatric patients to adult sizes. The bendable element is connected to the air supply interface near the first and second ends, and the user may modify the height of the bendable element by moving the first and second ends further or closer to the air supply interface. In one embodiment, the air supply interface may include first and second side slots through which the first and second ends of the bendable element extend. The user can pull or push the bendable element so that the user can move the first and second ends of the bendable element closer to or away from the first and second side slots, respectively.

So that the height and positioning of the bendable element about the user's face may be adjusted for various sizes and shapes of user's noses. Alternatively, an adjusting device may be secured to the air supply interface that includes first and second adjusters that engage with the bendable element near the first and second ends, respectively. Rotation of the first and second adjusters allow the user to adjust the height and positioning of the bendable element about the user's face.

In some embodiments, the housing or air supply interface includes a body that interfaces with the user's nasal passage via nostril interface tubes extending from the body. These tubes include a nasal interface element designed to aid in securing the device in place along with the bendable element that bends to match contours of the user's nose and holds its shape so as to secure a position of the air supply interface relative to the user's nose, thus eliminating the need for straps or headgear. The nasal interface elements are formed of an expandable, compressible material, meaning they can be compressed in order to insert them into the nostril, and once inserted they expand to apply pressure to the inner surfaces of the nostril opening to hold the device in place. Preferably, the contact is made at the end portion of the nostril so that only the section in the nostril covered by skin is contacted, thus avoiding the more sensitive nasal mucosa. Alternatively, the nostril interface elements are held against the outer edge of the nostrils.

These nasal interface elements can be formed of any suitable material which can be deformed, but are resilient in that they tend back to their original shape. A compressible foam is one material which may be well-suited for use in the invention. The interface element can be either permanently mounted to the interface tubes, or they may be removable and disposable so that they can be replaced after use. Thus, they can be mounted to the tubes via any suitable method. For example, they can be mounted via threading, frictional fit, or adhesive. However, other suitable methods of mounting the element to the tubes are contemplated and considered within the scope of the present invention.

The nasal interface elements of the present invention are ideally shaped in such a manner that they will form a seal or snug fit within the nostril of the user. This may mean they have more material on the bottom part toward the user's face, or that they may be specially formed to conform to the shape of the interior of the nostril. By exerting a small amount of pressure to the inside of the nostril, an additional advantage can be obtained by widening the passageway to allow more airflow. Furthermore, to enhance the securing of the device, the interface elements may include a mild adhesive on their exterior surface to hold them in place against the inner surfaces of the nostril. Such adhesive must be mild enough that the element can be easily removed by the user without causing significant discomfort or irritation or abrasion.

Optionally, these interface elements may contain an antibacterial agent to reduce the growth of contaminants. Once used, the user may replace the elements onto the tubes.

In various embodiments of the present invention, the interface tubes may further include a skirt surrounding the tube below the interface elements. Such skirts can be fitted against the outside of the nostril opening to help form a seal. Optionally, a mild adhesive can be disposed on the surface of the skirt which touches the outside edge of the nasal opening to help hold it in place.

In various embodiments of the present invention, the device also includes one or more flaps to assist in holding the device in place while in use. Side flaps are optionally included extending from the sides of the body of the device. An optional front flap may also be included. The front flap extends from the body of the device and is secured to the exterior surface of the nose of the user. It may be secured via a strip of tape, and adhesive on the underside of the flap, or by any other suitable method. This front flap holds the device in place during use.

In certain embodiments, the front flap may include resilient strips traversing the exterior of the nasal passageways. These strips can be deformed when applying the front flap to the nose via an adhesive, and will apply pressure tending to open the nasal passageways. A single one of such strips can be used. Alternatively, multiple strips can be used. Thus, the passageway is opened to allow more airflow, reducing the tendency of snoring in the user, and potentially reducing the air pressure required through the device to accomplish its purpose. Greater airflow may be enhanced by the combination of the strips and the expanding nasal interface elements, thus reducing air pressure requirements.

In a further embodiment, the nasal interface device configured to be positioned about a user's nose includes a bendable element including a bridge portion that corresponds to a bridge of the user's nose and first and second ends. The bendable element forms first and second platforms adjacent to the first and second ends. The nasal interface device further includes an adhesive secured to an underside of the bendable element. The bendable element bends to match contours of the user's nose and holds its shape so as to secure a position of the air supply interface relative to the user's nose.

In another aspect of the embodiment, the first and second platforms of the bendable element may support first and second lanyards of a cannula and/or a feeding tube. In further embodiments, each of the first and second ends of the bendable element include one of a protrusion, a button, and a clasp that attaches to first and second sides, respectively, of the bendable element.

In yet another embodiment, the nasal interface device may be positioned onto a pair of glasses to maintain the positioning of a cannula and/or a feeding tube relative to the user's nostrils. The bridge portion of the bendable element may be received by the pad arms carrying the nose pads of the glasses.

Still other objects and advantages of the present invention will become readily apparent to those skilled in the art from the following detailed description, wherein it is shown and described only the preferred embodiments of the invention, simply by way of illustration of the best mode contemplated of carrying out the invention. As will be realized, the invention is capable of other and different embodiments and its several details are capable of modifications in various obvious respects, without departing from the invention. Accordingly, the drawings, wherein like reference numerals represent like features, and description are to be regarded as illustrative in nature and not as restrictive.

BRIEF DESCRIPTION OF THE DRAWINGS

FIG. 1 shows an embodiment of the nasal interface device of the present application.

FIG. 2 shows another embodiment of the nasal interface device of the present application, having optional side and front straps for mounting the device.

DETAILED DESCRIPTION OF THE DISCLOSURE

Figure 3:
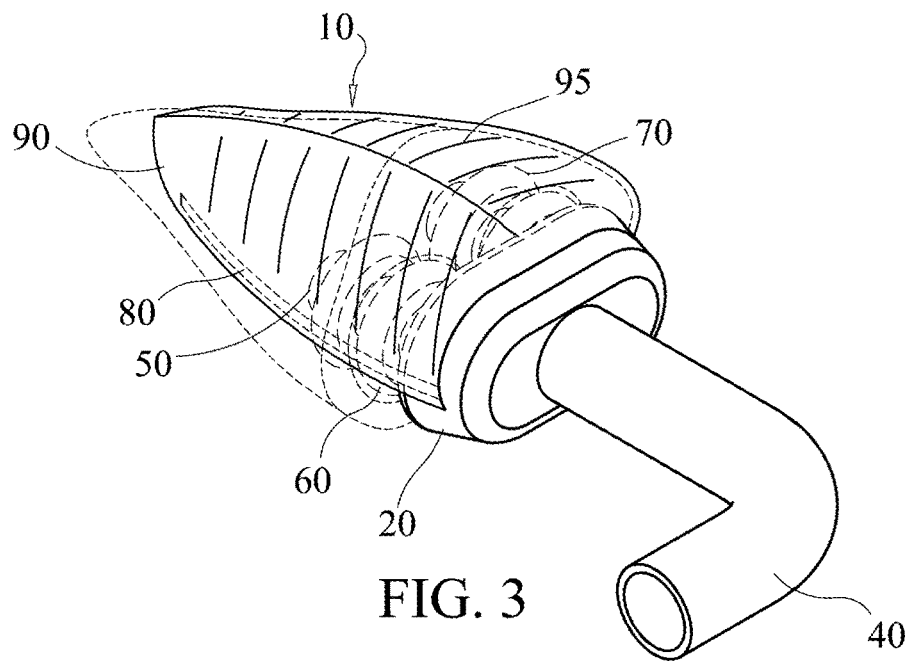
FIG. 3 shows an embodiment of FIG. 2 as mounted on a user's nose.
Figure 4:
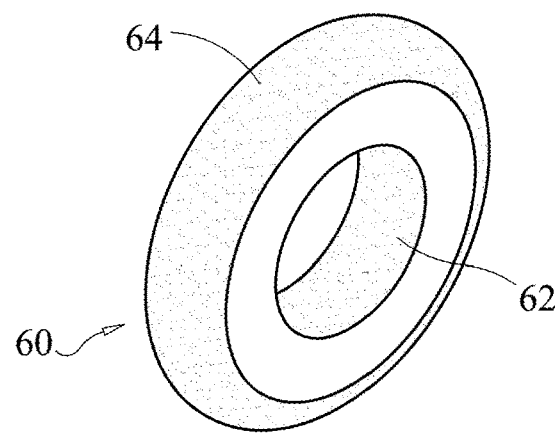
FIG. 4 shows an embodiment of the nasal interface element used in the embodiments of the nasal interface devices of FIGS. 1 and 2.

While this invention is susceptible of embodiments in many different forms, there are shown in the drawings and will herein be described in detail, preferred embodiments of the invention with the understanding that the present disclosure is to be considered as an exemplification of the principles of the invention and is not intended to limit the broad aspect of the invention to the embodiments illustrated.

The present invention is a strapless nasal interface device 10 suitable for use with a CPAP or BIPAP device, or any other ventilator type device. The device 10 includes an interface body 20 having an interior cavity. The cavity is fluidly connected to an air tube 40 extending from the body 20 for use with a CPAP or other device. The body 20 ideally includes exhalation holes 30 to enable expelled air to escape the device 10.

The device 10 further includes at least one nostril interface tube 50 extending from the body 20 to interface with the nasal passages of a user or a person. Preferably, two such tubes 50 are included. Surrounding the tubes are compressible expandable nasal interface elements 60. These elements 60 are formed such that they can be compressed to fit within the nostril of the user, after which they expand to make contact with the interior of the nostril at the inner edge of the nostril to hold the interface tube 50 in place within the nostril. Thus, the need for straps or headgear in conjunction with the device is eliminated.

In various embodiments of the present invention, the interface elements 60 are permanently mounted to the interface tubes 50. However, in various other embodiments, the interface elements 60 are removably mounted to the tubes 50. If removably mounted, the interface elements 60 may be mounted to the tubes 50 by any suitable means. For example, they may be threaded, frictionally fit, or adhered with an adhesive 62.

Interface elements 60 can be formed of any suitable material. In certain embodiments, they are formed of an expandable, compressible foam. Preferably, the elements 60 have an anti-bacterial agent. Optionally, elements 60 may include a mild adhesive 64 on the outer surface to make contact with the skin on the interior of the nostril. Ideally, elements 60 form a seal within the nostril. Ideally, they are shaped to optimize such a seal. For example, they may be formed to conform to the interior shape of the nostril so as to form a proper fit.

In various embodiments of the present invention, a skirt 70 is also included. The skirt 70 is disposed on the nostril interface tube 50 between the interface element 60 and the interface body 20. The skirt interfaces with the end of the nostril opening to help aid in sealing the air passage. Optionally, a mild adhesive can be disposed on the surface 75 of the skirt 70 adjacent the rim of the nostril opening to further seal the passageway.

In various further embodiments, the device 10 includes one or more flaps in order to further secure it on the user. For example, in certain embodiments, side flaps 80 extend from the body 20. The side flaps 80 have an adhesive thereon to adhere the flaps to the exterior of the nose, further securing it. Side flaps 80 may be mounted to the interface body 20 by any suitable method, such as via a groove in the interface body 20 allowing an end of flap to be inserted. Such a fit may be a friction fit, or it may be a dovetail groove. However, any other suitable method of attachment is contemplated as within the scope of the invention.

Additionally, an optional front flap 90 may extend from the interface body 20. The front flap 90 covers an exterior portion of the nose. It can be mounted to the nose via any suitable method. For example, a separate strip of tape or adhesive may be used. In certain embodiments, it may be mounted via an adhesive on the underside of the front flap 90. Thus, the device 10 is further secured to the nose of the user. Front flap 90 may be mounted to the interface body 20 by any suitable method, such as via a groove in the interface body 20 allowing an end of flap 90 to be inserted. Such a fit may be a friction fit, or it may be a dovetail groove. However, any other suitable method of attachment is contemplated as within the scope of the invention.

In various embodiments, the front flap 90 of the device 10 further includes tension bows or strips 95. These strips 95 are formed of a resilient material. Thus, the strips 95 may be deformed when adhered to the exterior of the nose via an adhesive on the underside of the front flap 90, after which they apply pressure tending to expand the nasal passageway. Thus, the passageways are expanded, relieving a tendency of snoring and potentially reducing the air pressure required for the user's purposes. While a single such strip 95 can be used, in certain embodiments multiple strips 95 are used to open the passageway along an entire portion of the passageway. The front flap 90 can be used without side flaps 80, or in conjunction therewith.

In various other embodiments, the present invention includes a strapless nasal interface device 100 having an interface body 105 having an internal cavity 110. The cavity 110 is in communication with an air tube 115 which extends from the body 105. The air tube 115 is preferably rotatably attached to the interface body 105 at a first point of attachment 120. Ideally, this point of attachment 120 allows the air tube 115 to rotate 360 degrees, yet maintains a substantially leak-proof connection regardless of how the air tube 115 is oriented with respect to the interface body 105. A sealing o-ring may be incorporated to facilitate the rotatable mounting. This first point of attachment 120 may be located at any suitable position on interface body 105, however, in a preferred embodiment it is located on a front wall which is adjacent the wall on which nostril interface tubes 135 are located such that the air tube 115 extends out perpendicular to the plane of the face and away from the face, thus keeping air tube 115 and air supply tube 125 from rubbing against the face of the user.

Preferably, the device 100 comprises at least one exhalation hole, and preferably a plurality of exhalation ports or holes 122 which are sized to allow exhaled air to pass therethrough, but which are sized so that they do not substantially depressurize the cavity 110 of the interface body 105. Exhalation holes 122 can be placed in any suitable location on the interface body 105. For example, they may be placed on the side opposite of where nostril interface tubes 135 are located, or on the top side of the interface body 105 near the first point of attachment 120, or in both locations, or in any other suitable location. In certain embodiments, 35 to 40 exhalation holes sized at about 0.023 inches each may be suitable to enable carbon dioxide rich exhalation air to leave the cavity 110, yet such holes 122 are small enough such that air pressure intended to pressurize the nasal passage is maintained. In another embodiment, hole sizes may be approximately 0.02 inches in diameter, and about 78 of them may be suitable. However, any size, number, and configuration of exhalation holes 122 which function as described is suitable and contemplated within the scope of the present invention.

In various embodiments, the air tube 115 is also attached to an air supply tube 125. Preferably, this is a removable attachment. Optionally, the connection at a second attachment point 130 between the air tube 115 and the air supply tube 125 also allows rotation while maintaining a leak-proof connection. Ideally, 360 degrees of rotation is enabled. In certain embodiments, the air tube 115 is bent somewhere along its length, such that the planes of rotation at the two attachment points 120 and 130 are different planes of rotation. For example, if the air tube is bent by about 90 degrees, the planes of rotation will be substantially orthogonal with respect to one another. In some embodiments, one plane of rotation will be parallel to the face of the user, and the other will be perpendicular to the user. This allows for a great degree of freedom of movement of the user without compromising the integrity of the seal formed between the device and the user's nostrils.

In various embodiments, the device includes at least one nostril interface tube 135 having an internal passage extending from the interface body 105 to the nostrils of a user. Preferably, there are two such tubes or nostril interface elements 135 extending to the nostrils of a user. In certain embodiments, the nostril interface elements 135 include an upper cushion 140, which is a radial protrusion, preferably formed of compressible material such that the upper surface of the cushion can be compressed against the outer edge of the nostril to help form a seal with the nostril of the user. Ideally, nostril interface tubes 135 are each formed as a single integral piece which can be attached and removed from the interface body 105.

Preferably, the nostril interface elements 135 also include a lower radial element 145 which is a radial protrusion adapted to be urged toward the upper cushion 140 and to compress the upper cushion 140 to aid in forming a seal between the upper cushion 140 and a user's nostril when the device 100 is worn by a user. In certain embodiments, the lower radial element 145 includes an internal substantially rigid rim 152 adapted to aid in compressing the upper cushion 140 when the device 100 is worn by a user.

Ideally, the nostril interface elements 135 have substantially non-porous surfaces. For example, they may be formed entirely of a non-porous material such as silicone or any other suitable material. Alternatively, at least the exposed surfaces of the nostril interface elements 135 are coated with a non-porous material such as silicone, or any other suitable material. In certain embodiments, the nostril interface elements 135 are removably attached to the interface body 105, such as via a snap fit, frictional fit, threading, or any other suitable method. Thus, they can be removed for cleaning or replacement.

The device 100 includes a facial patch 150. The facial patch can be adhered to the face of a user. Preferably, the facial patch 150 is a nose cover 150 which adheres to the nose of a user. The nose cover 150 preferably includes an adhesive on its bottom surface to removably adhere to the skin of the user's nose. The adhesive is ideally suitable for use on skin and removable. This nose cover 150 is ideally disposable and replaceable.

The nose cover 150 is ideally formed of a flexible material. Optionally, a bendable element 155 is included as part of the nose cover 150 which may be embedded within it or on one of its surfaces. The bendable element 155 is formed of a material which can be bent to fit the contour of the nose and hold its shape so as to help the nose cover 150 adhere to the nose. The bendable element may be formed of any suitable material, such as a metal as aluminum, or any other material with suitable properties.

Figure 5:
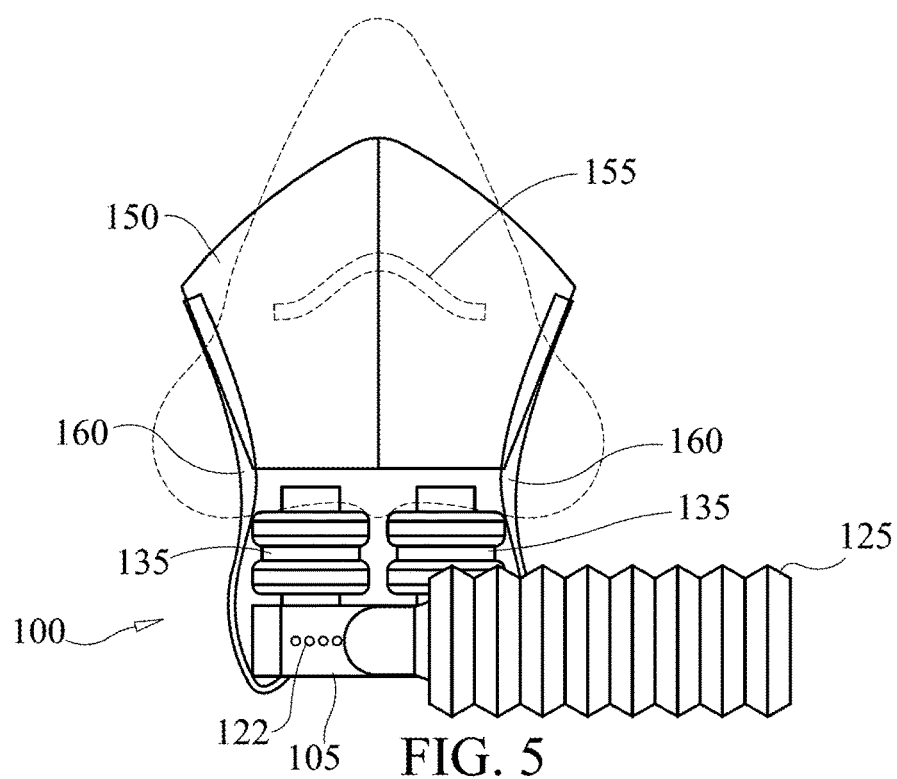
FIG. 5 shows another embodiment of the nasal interface device of the present application.
Figure 6:
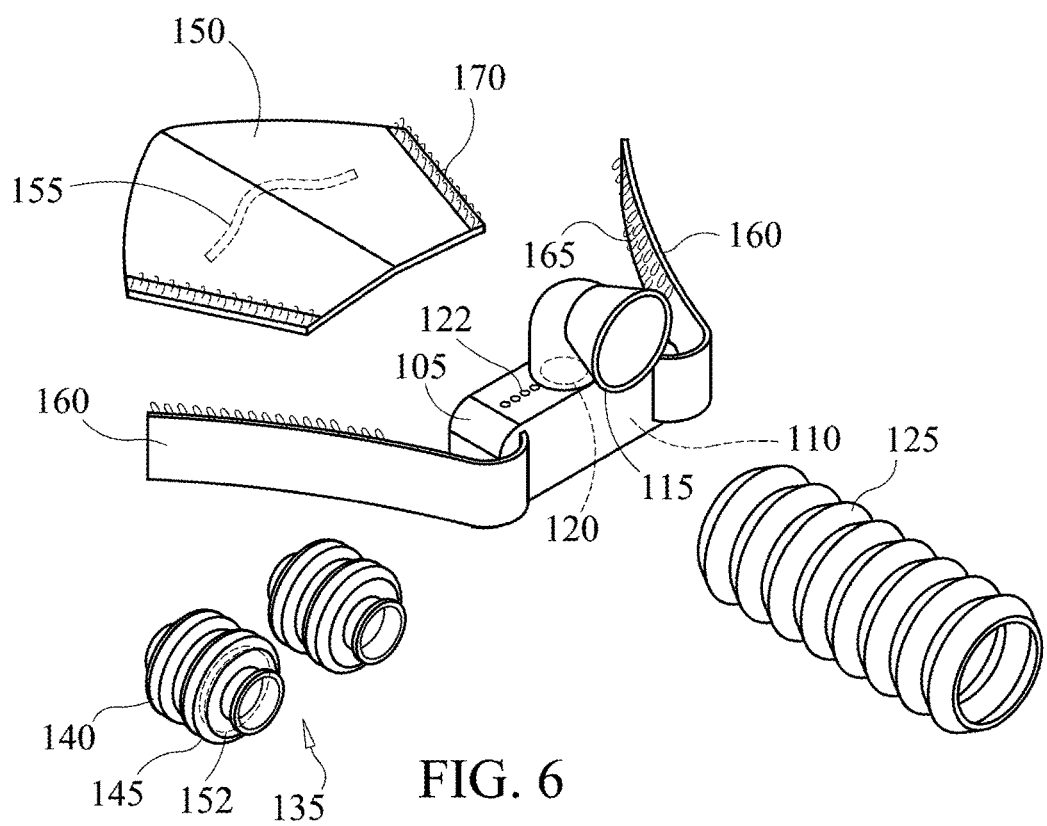
FIG. 6 shows an exploded view of the embodiment of FIG. 5.
Figure 7:
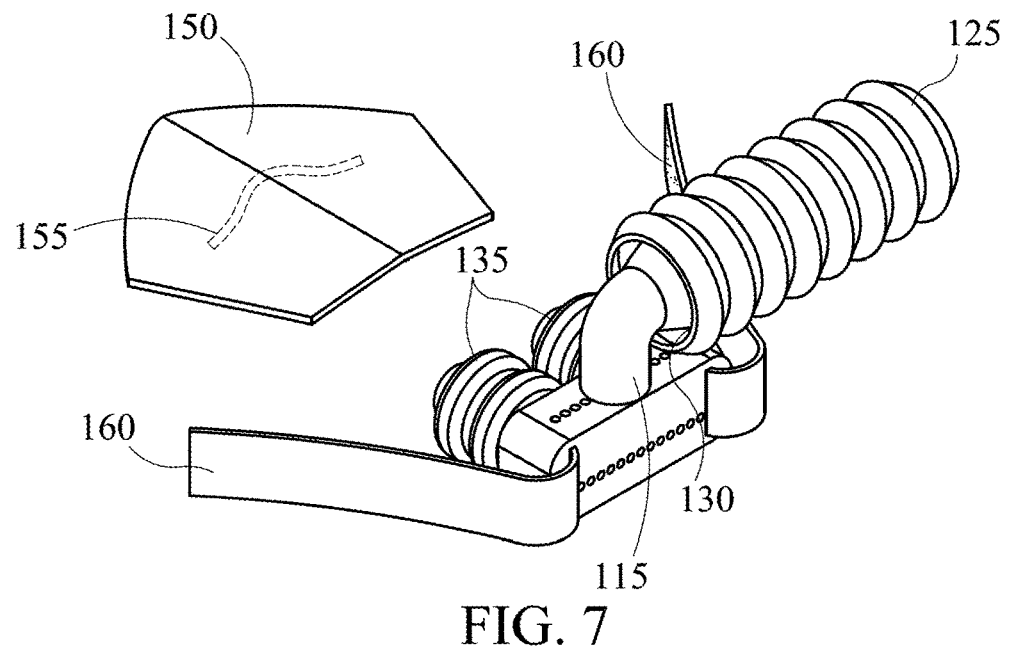
FIG. 7 shows a perspective view of a further embodiment of the nasal interface device of the present application.

In the embodiment illustrated in FIGS. 5 and 6, one or two attachment flaps 160 are connected to the nasal interface body 105 to hold the device 100 in place properly. They secure to the surface of the nose cover 150. Any suitable manner of removable attachment is contemplated. For example, hook and loop attachment in which one element of the hook and loop material 165 is attached to the flaps 160, and the other element of the hook and loop material 170 is attached to the surface of the nose cover 150. However, an adhesive or other manner of attachment can be used. Ideally, the flaps 160 extend around the sides of the interface body 105 and hold the device 100 snug against the nostrils. In this way, no straps around the head of the user are required.

Figure 8:
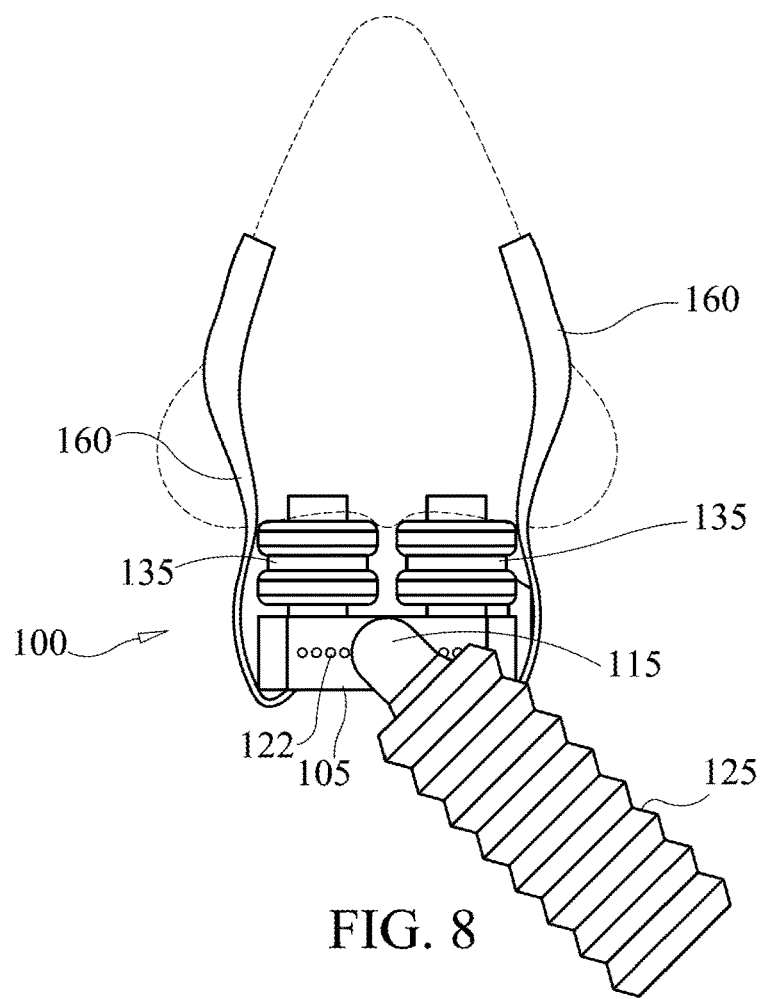
FIG. 8 shows another embodiment of the nasal interface device of the present application.

In an alternate embodiment, the nostril interface elements 135 may include a magnet or iron or nickel bearing material, and they may be secured to the nose via magnets on the external surface of the nose. In a further alternate embodiment, as shown in FIG. 8, the nose cover 150 may be eliminated and one or more flaps 160 may be adhered directly to the outer surface of the nose of the user.

FIGS. 9-12 illustrate a further embodiment of a strapless nasal interface device 300 suitable for use with a CPAP or BIPAP device, or with any other ventilator type device. The device 300 includes an air supply interface 302 defining an interior cavity or chamber 304, an intermediate air tube 306, and an air supply tube 310 extending therefrom.

Figure 10:
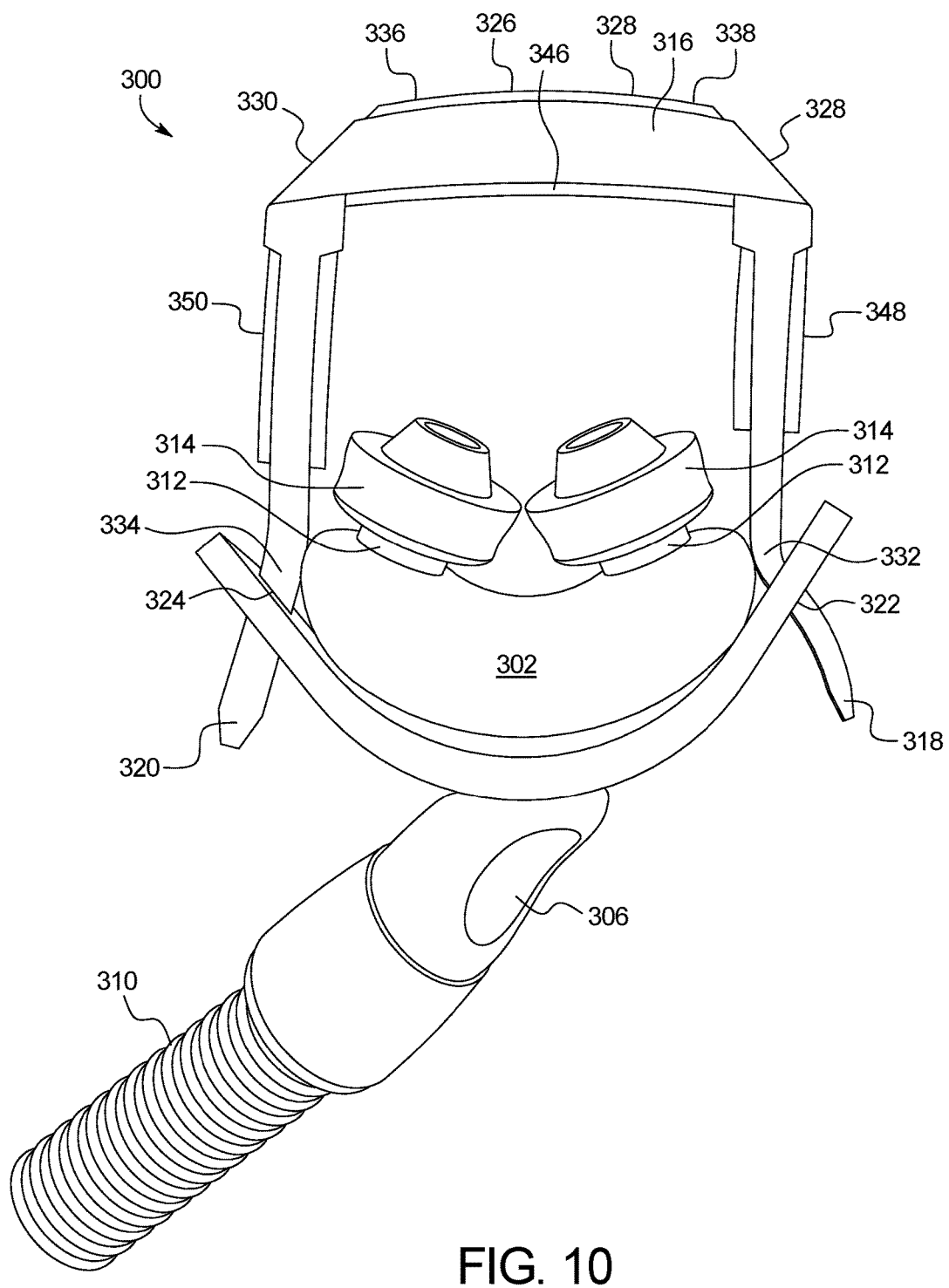
FIG. 10 is a front elevational view of the nasal interface device of FIG. 9.

The device 300 includes one or two nostril interface tubes 312 extending from a body 313 of the air supply interface 302 to engage with the nasal passages of the user as described with respect to previous embodiments. Referring to FIG. 10, compressible expandable nasal interface elements 314 surround the tubes 312 and are formed such that they can be compressed to fit within the nostril of the user, after which they expand to make contact with the interior of the nostril at the inner edge of the nostril to hold the interface tube 312 in place within the nostril. Each of the interface tubes 312 may also include a skirt (see FIG. 1) to aid in sealing the air passage.

Figure 9:
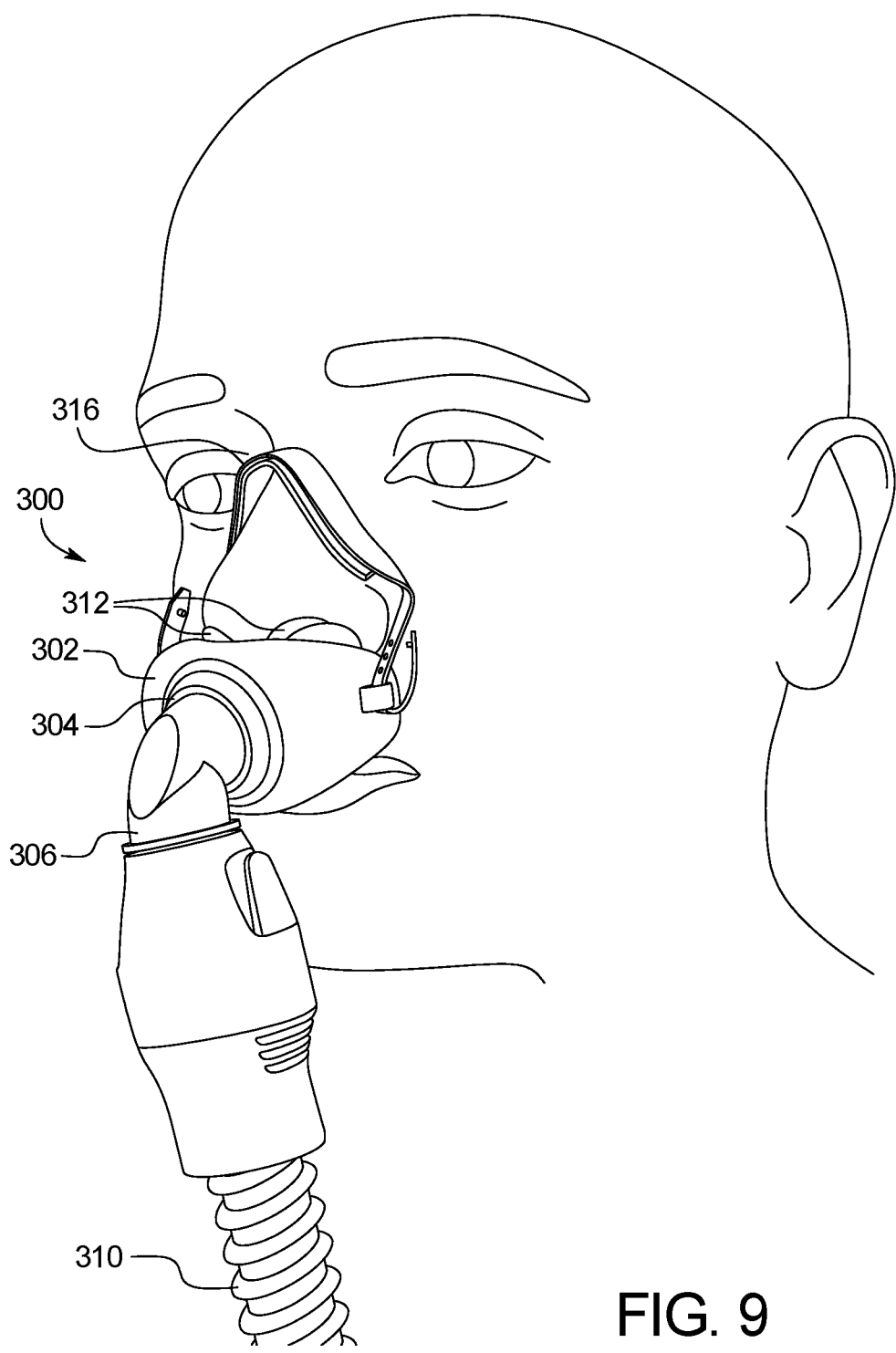
FIG. 9 is a perspective view of a further embodiment of the nasal interface device of the present application.
Figures 11, 11A:
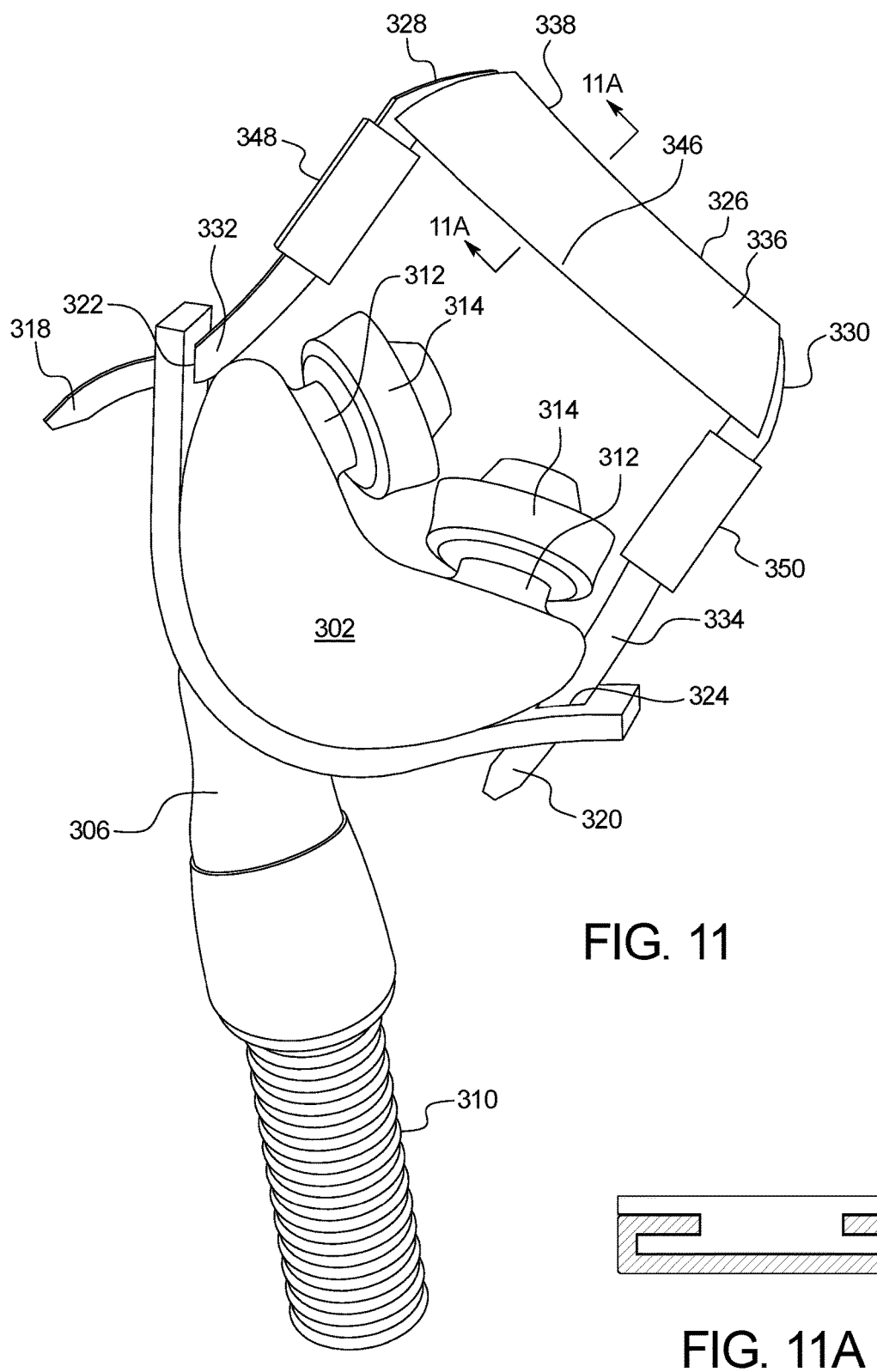
FIG. 11 is a rear elevational view of the nasal interface device of FIG. 9.
FIG. 11A is a cross-sectional view generally taken along lines 11A-11A shown in FIG. 11.

Seen best in FIGS. 10 and 11, a bendable element 316 is secured to the air supply interface 302 and is sufficiently flexible so that its shape corresponds to contours of the user's face as seen in FIG. 9. First and second ends 318, 320 of the bendable element 316 engage with first and second slots 322, 324 on the interface body 313 to hold the air supply interface 302 in position relative to the user's nose as the bendable element 316 is secured to the user's face.

Figure 12:
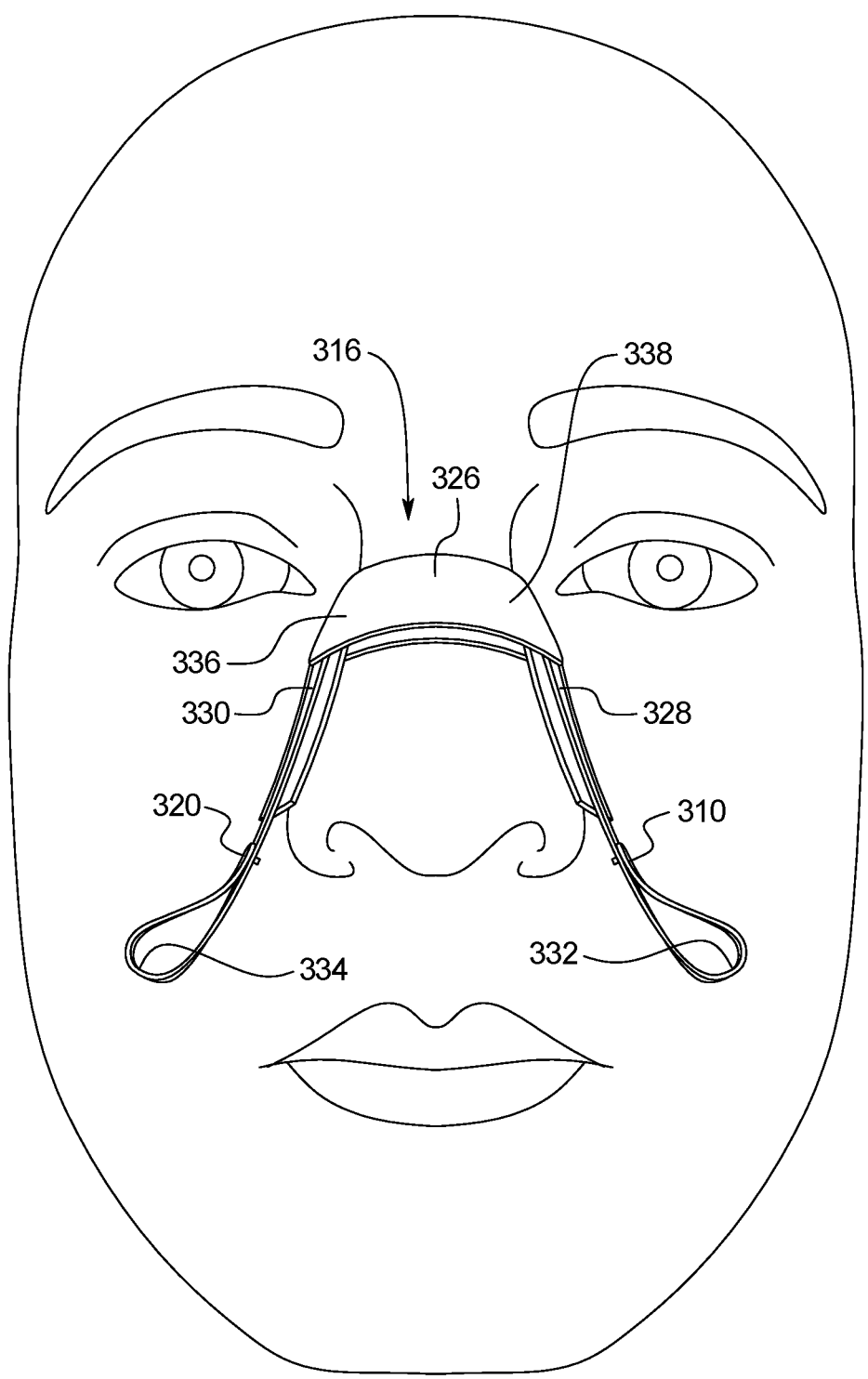
FIG. 12 is a front elevational view of a bendable element used in the nasal interface device of FIG. 9.

The bendable element 316 illustrated in FIG. 12 is a metallic strip including bends that correspond to contours of the user's nose and face. The plasticity of the material of the bendable element 316 is deformable so that it bends to match contours of the user's nose while maintaining its shape so as to secure the positioning of the air supply interface 302 relative to the user's nose. The material of the bendable element 316 may be aluminum or other suitable material.

A first bend 326 of the bendable element 316 corresponds to the bridge area of a user's nose. Second and third bends 328, 330 define first and second side portions 336, 338, respectively, of the bendable element 316 that are seated against the sides of the user's nose. Fourth and fifth bends 332, 334 adjacent to first and second ends 318, 320 of the bendable element 316 engage the body 313 of the air supply interface 302. While the illustrated embodiment includes five bends, the bendable element 316 may be free from bends yet be shaped to conform to the user's face, or may include any number of bends necessary to conform to the user's face and/or to engage the air supply interface 302.

In the embodiment illustrated in FIG. 9, the first and second ends 318, 320 of the bendable element 316 are threaded through the first and second slots 322, 324 on the interface body 313 and moveable so that the position of the bendable element 316 can be adjusted for varying sizes and heights of users' noses. As shown in FIG. 12, the first and second ends 318, 320 may include protrusions that are received by openings in the first and second side portions 336, 338, although other suitable fasteners such as, but not limited to, buttons and/or clasps for securing the first and second ends 318, 320 to first and second side portions 336, 338 of the bendable element 316 may be used. During use, the user can adjust the height of the bendable element 316 so that it is positioned comfortably and appropriately on the user's nose while the air supply interface 302 is positioned at the user's nostrils.

Figure 18:
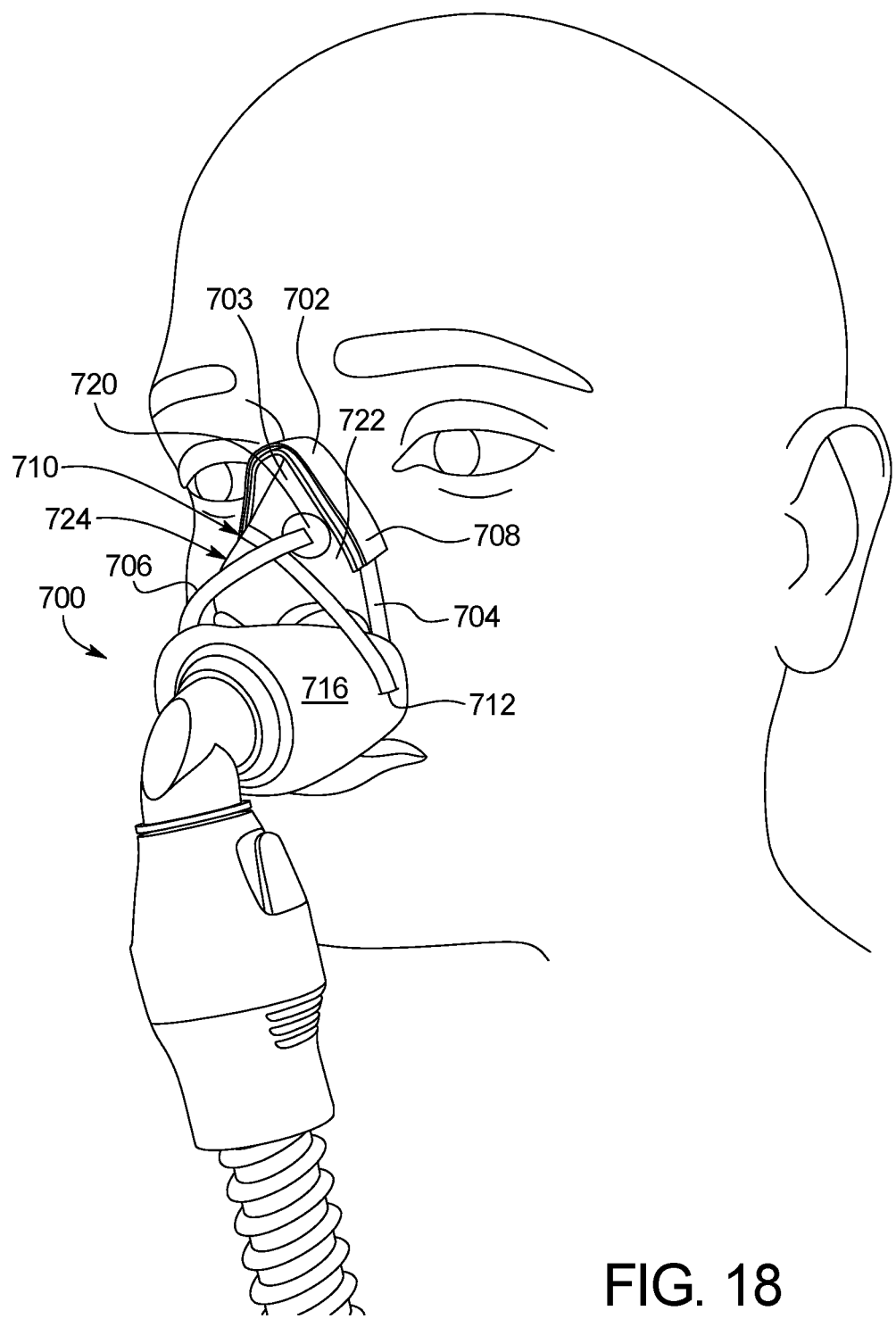
FIG. 18 is a perspective view of another embodiment of the nasal interface device of the present application.
Figure 19:
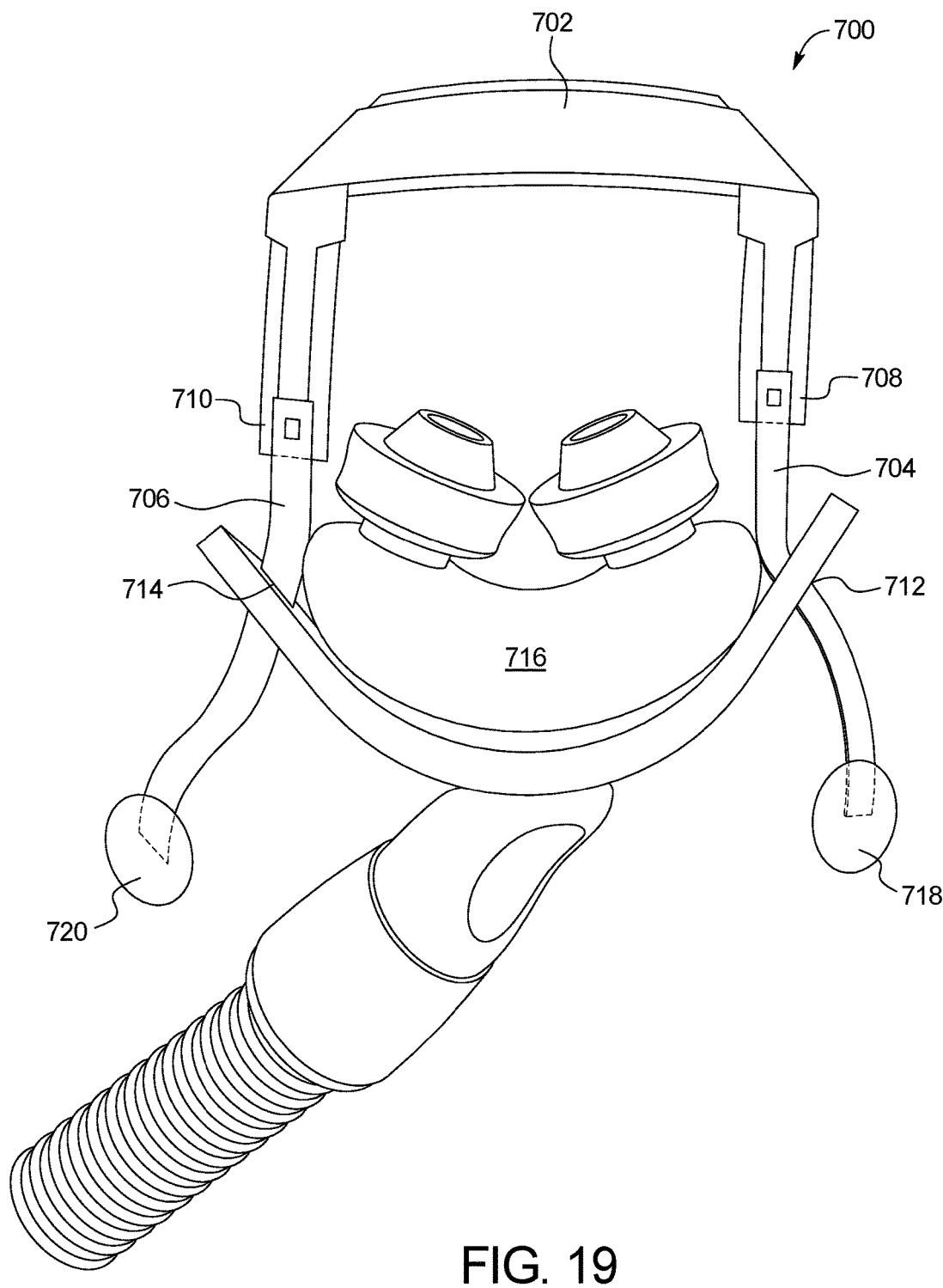
FIG. 19 is a front elevational view of the nasal interface device of FIG. 18.
Figure 20:
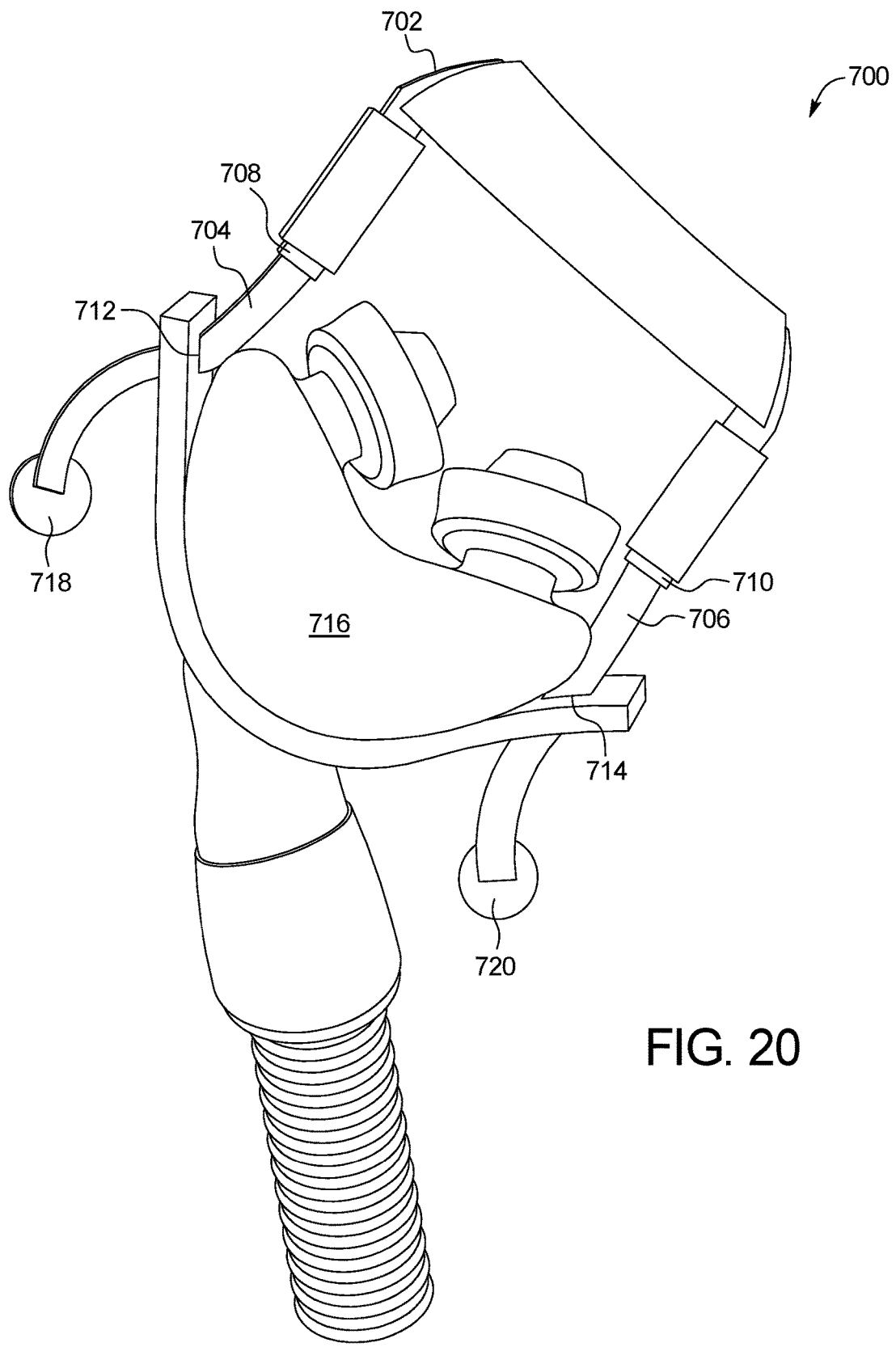
FIG. 20 is a rear elevational view of the nasal interface device of FIG. 18

Referring to an alternative embodiment illustrated in FIGS. 18-20, a strapless nasal interface device 700 secures a bendable element 702 to the bridge area 703 of the user's nose using first and second elastic members 704, 706. First ends of the first and second elastic members 704, 706 are secured to first and second ends 708, 710, respectively, of the bendable element 702. In the illustrated embodiment, the first and second elastic members 704, 706 are threaded through first and second slots 712, 714, respectively, within the interface body 716. In other embodiments, the first and second elastic members 704, 706 may be attached to the sides of interface body 716 by any suitable means, such as, for example, through a slotted surface on the interface body 716 or any other attachment means as described with respect to other embodiments of the present application.

In a preferred embodiment, each elastic member 704, 706 is a rubber or other suitable material having a minimum Young's modulus of 0.01 to 0.1 GPa. In some embodiments, each elastic member 704, 706 may have a length of about 3 cm to about 4 cm and a width of about 1 cm to 1.5 cm.

At second ends of the first and second elastic members 704, 706, first and second adhesive members 718, 720 adhere to first and second sides 722, 724 of the user's nose. Each adhesive member 718, 720 may comprise an elastic surgical tape material. One example material is a foam adhesive tape that conforms easily to facial features such as 3M Microfoam (St. Paul, Minn.). In some embodiments, each adhesive member 718, 720 may have a length of about 3 cm to about 6 cm and a width of about 1 cm to 1.5 cm.

During use, the user first inserts the interface body 716 and/or nose pillows adjacent to the nose or nostrils. The user then adjusts the positioning of each elastic member 704, 706 within the respective slot 712, 714 so that each adhesive member 718, 720 is positioned on the side 722, 724 of the nose and is taut between first and second ends 708, 710, respectively, of the bendable element 702 and the adhesive members 718, 720. In the embodiment illustrated in FIG. 18, the first and second adhesive members 718, 720 cross the user's nose and are secured to the opposite sides 724 and 722, respectively. In other embodiments, the first and second adhesive members 718, 720 are secured to the adjacent sides 722 and 724. Due to the stretching of the elastic members 704, 706 and the adhesive members 718, 720, the interface body 716 fits snug against the user's nose without the need for straps extending around the head or extending along the cheeks of the user. The lack of straps and additional attachment means provides a more comfortable sleep for the user due to the elimination of the straps as well as the minimization of the unit altogether. Further, the combination of the elastic members 704, 706 in conjunction with the metallic bendable element 702 secure the seal of the interface body 716 at the user's nose and maintains the interface body 716 in close proximity to the nostrils. Simultaneously, the elastic members 704, 706 and the bendable element 702 allow the user to conform and adjust the device about the user's face and as necessary to maintain the seal.

Figure 21:
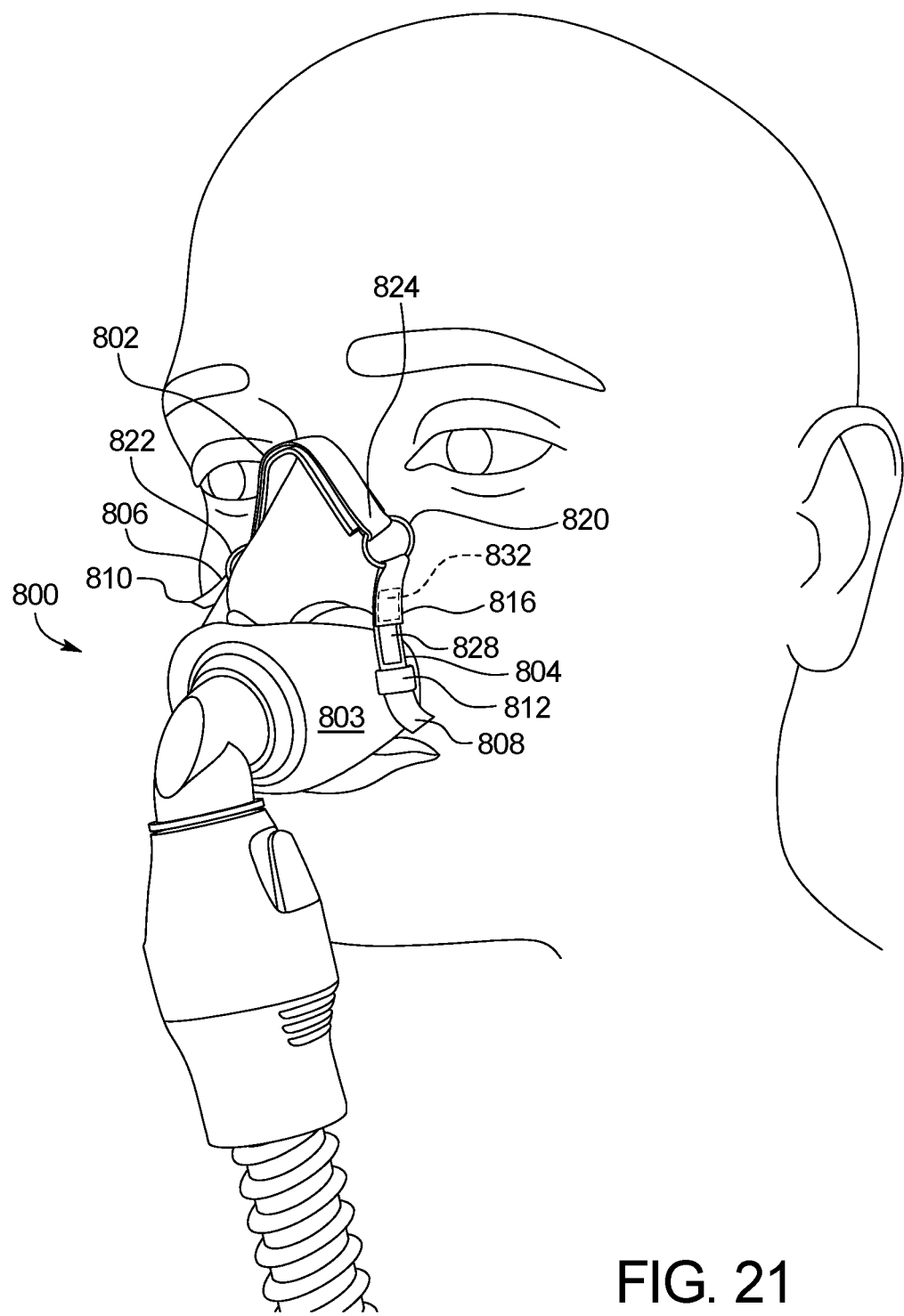
FIG. 21 is a perspective view of a further embodiment of the nasal interface device of the present application.
Figure 22:
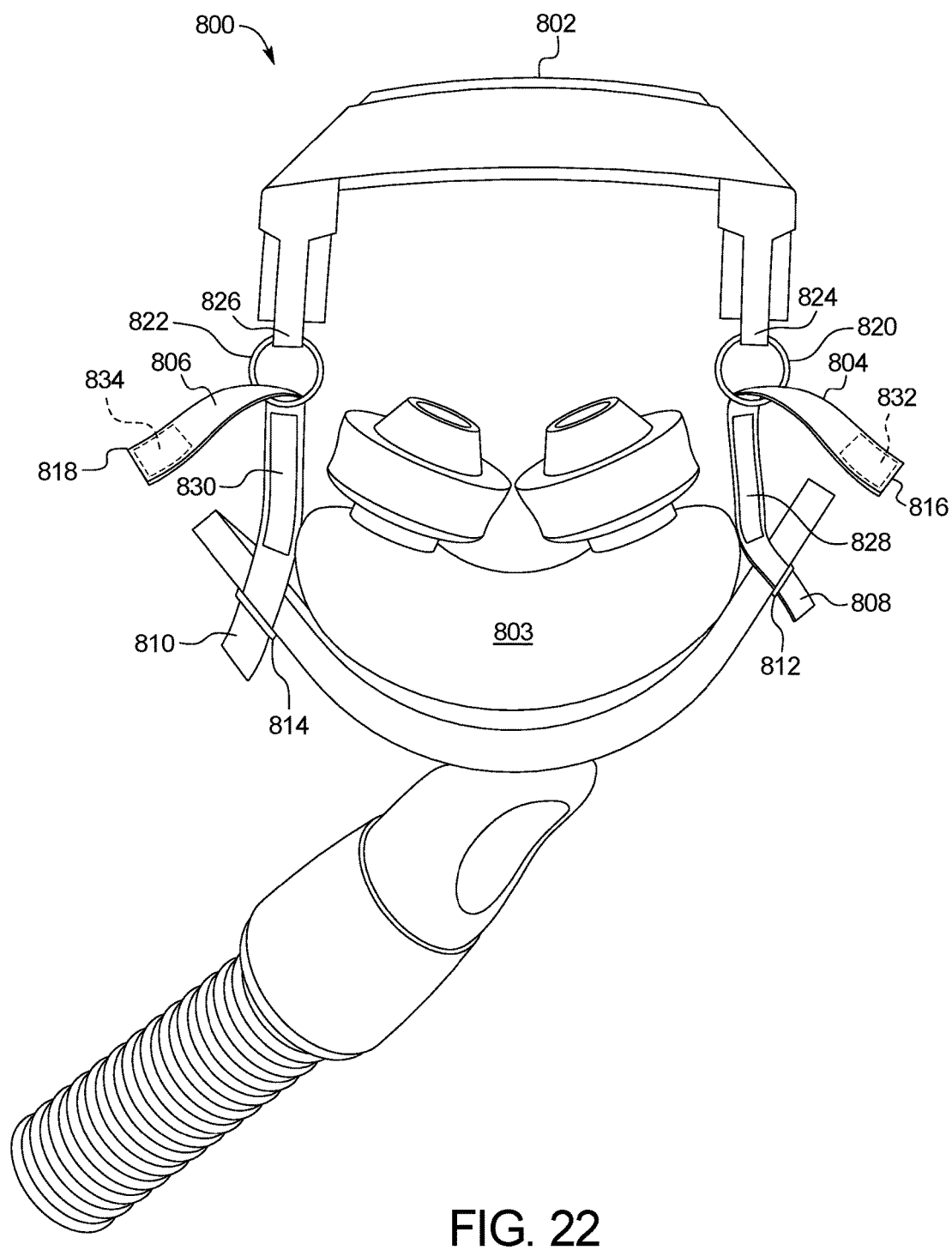
FIG. 22 is a front elevational view of the nasal interface device of FIG. 22.

FIGS. 21 and 22 illustrate a strapless nasal interface device 800 including a bendable element 802 secured to the interface body 803 via first and second elastic members 804, 806. In this embodiment, first and second elastic members 804, 806 are positioned such that first ends 808, 810 are adjacent to first and second slotted surfaces 812, 814, respectively, of the interface body 803. In other embodiments, the first and second elastic members 804, 806 may extend through first and second slot within the interface body 803, or the first and second elastic members 804, 806 may attach to the interface body 803 through any other suitable attachment means, particularly as described with respect to other embodiments of the present application.

Second ends 816, 818 of the first and second elastic members 804, 806 are threaded through first and second rings 820, 822, respectively, that are secured to the first and second ends 824, 826, respectively, of the bendable element 802. The first and second ends 824, 826 of the bendable element 802 may be bent in a folding fashion to provide a hooking surface to receive the first and second rings 820, 822, respectively. Other connection means may also be used.

In one embodiment, each of the first and second elastic members 804, 806 include a first hook and loop fastener surface 828, 830 on at least one side of each first and second elastic members 804, 806 adjacent to the interface body 803 and a second hook and loop fastener surface 832, 834 on second ends 816, 818 of the first and second elastic members 804, 806. During use, the first and second elastic members 804, 806 are taut between the first and second slots 812, 814 of the interface body 803 and the second hook and loop fastener surface 832, 834 of the first and second elastic members 804, 806.

Similar to the device described above, the combination of the elastic members 804, 806 in conjunction with the metallic bendable element 802 secure the seal of the interface body 803 at the user's nose and maintains the interface body 803 in close proximity to the nostrils. Simultaneously, the elastic members 804, 806 and the bendable element 802 allow the user to conform and adjust the device 800 about the user's face and as necessary to maintain the seal. In some embodiments, the strapless nasal interface device 800 delivers pressures between about 4 and about 20 cmH$_2$O.

Figure 23:
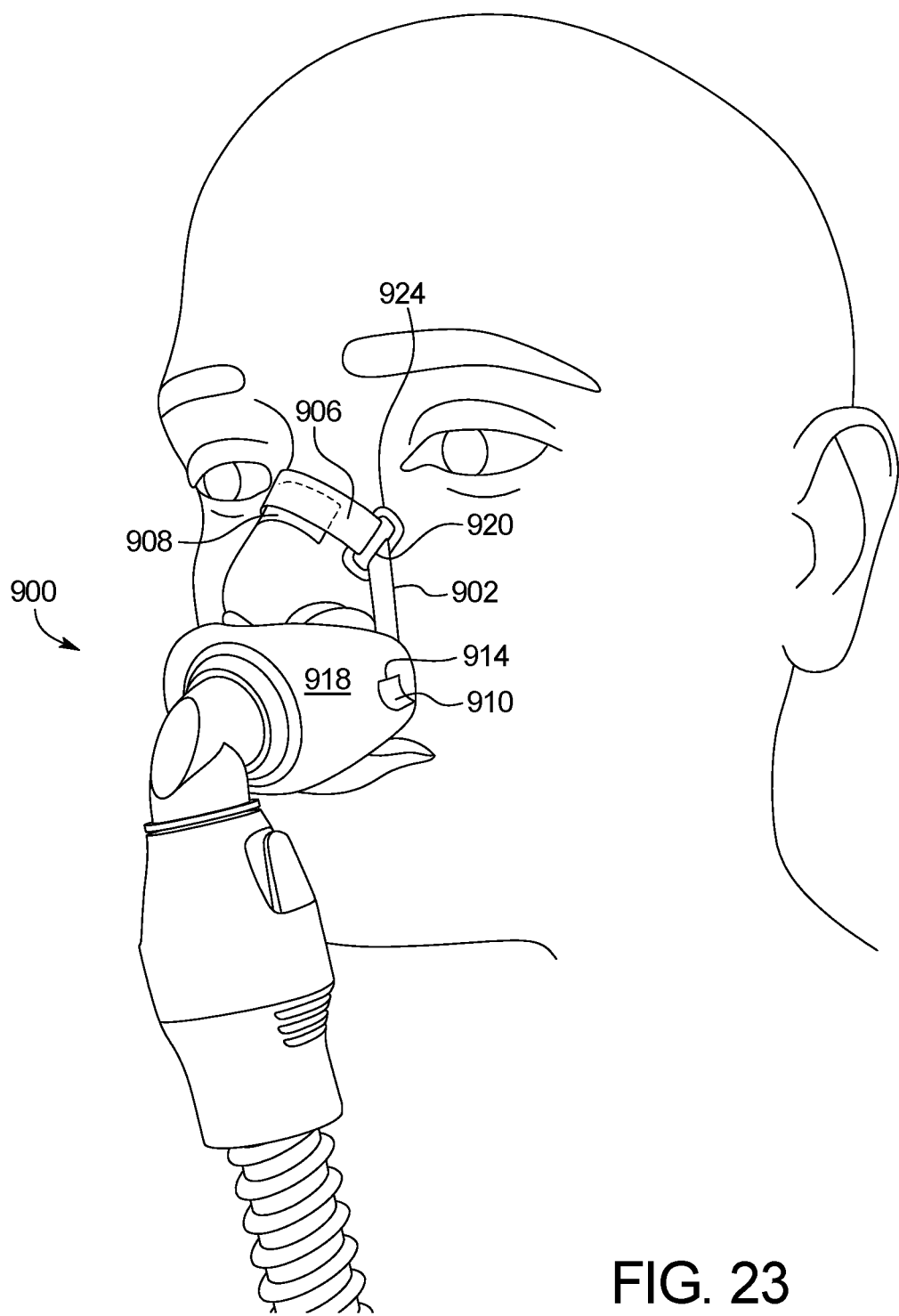
FIG. 23 is a perspective view of a further embodiment of the nasal interface device of the present application.
Figure 24:
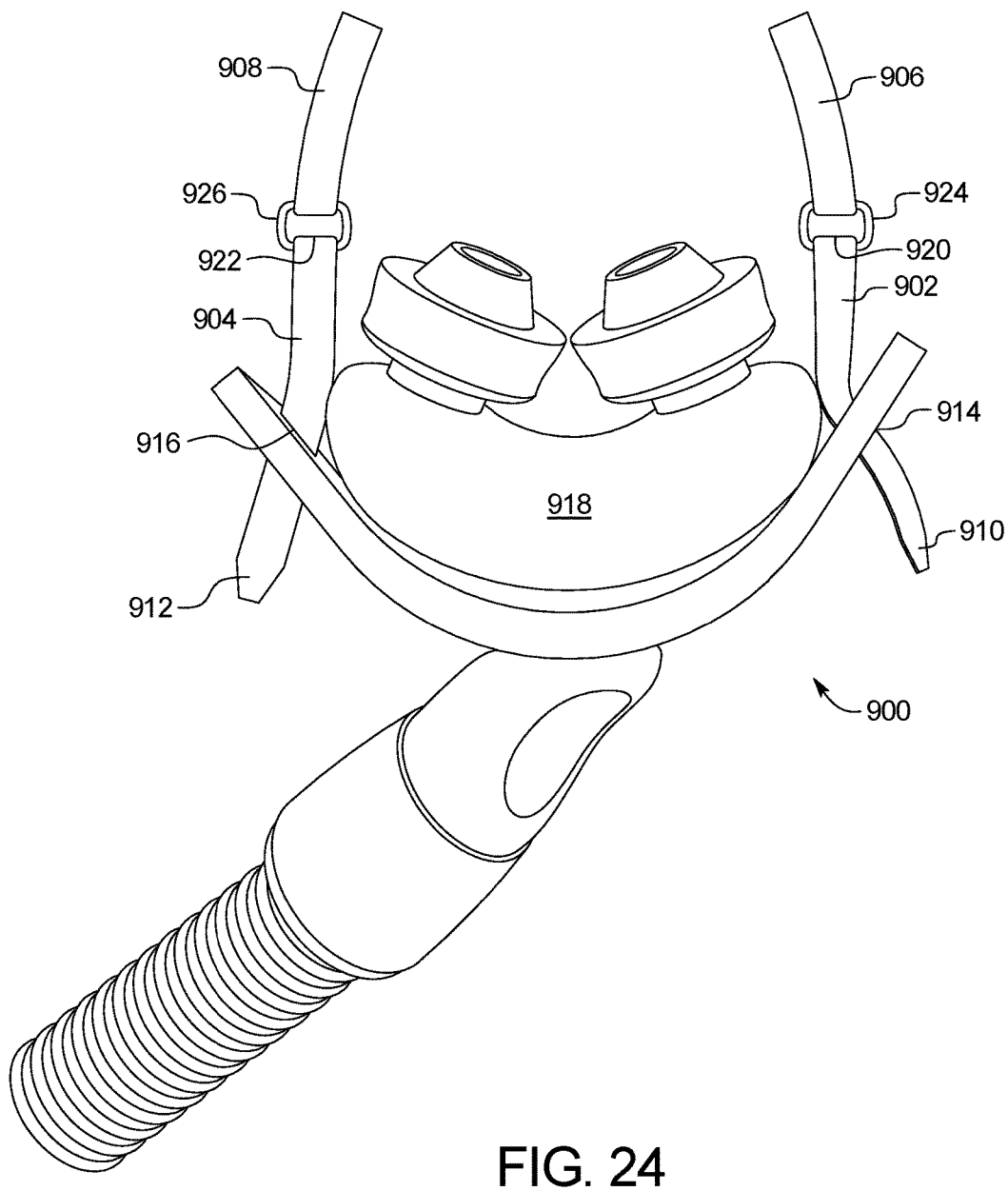
FIG. 24 is a front elevational view of the nasal interface device of FIG. 22.

In a still further embodiment illustrated in FIGS. 23 and 24, a strapless nasal interface device 900 is secured to the user's nose by first and second elastic members 902, 904 and corresponding adhesive members 906, 908. More specifically, the first and second elastic members 902, 904 extend through first and second slots 914, 916, respectively, of the interface body 918, although any suitable attachment means may be used. In the illustrated embodiment, the first and second slots 914, 916 are sufficiently narrow so as to secure first ends 910, 912 of the first and second elastic members 902, 904 in place.

First and second adhesive members 906, 908 are attached to second ends 920, 922 of the first and second elastic members 902, 904, respectively. Referring to FIG. 24, each elastic member 902, 904 is secured to the respective adhesive member 906, 908 by a ring 924, 926 or other suitable securing mechanism. The adhesive member 906, 908 may comprise an elastic surgical tape material. One example material is a foam adhesive tape that conforms easily to facial features such as 3M Microfoam (St. Paul, Minn.).

During use, the user first inserts the interface body 918 and/or nose pillows adjacent to the nose or nostrils. The user then adjusts the positioning of each elastic member 902, 904 within the slot 914, 916 to position each adhesive member 906, 908 on the side of the nose so that each elastic member 902, 904 is taut between the slot 914, 916 and the adhesive member 906, 908. In the embodiment illustrated in FIG. 23, the user adheres the first adhesive member 906 to the bridge area of the user's nose, and then adheres the second adhesive member 908 to the bridge area of the user's nose overlapping with the first adhesive member 906. In other embodiments, the interface device 900 may be used to position a cannula that is connected to an oxygen tank so that the nasal prongs of the cannula are at the user's nostrils. In a further embodiment, the nasal interface device may be used to maintain the positioning of a feeding tube at the user's nostrils. Any of the nasal devices described herein may be in fluid communication with a ventilator, a continuous positive airway pressure (CPAP) machine, and a bilevel positive airway pressure (BiPAP) machine.

Similar to the embodiments mentioned above, the stretching of the elastic members 902, 904 and the adhesive members 906, 908 allows the interface body 918 to fit snugly against the user's nose without the need for straps extending around the head or extending along the cheeks of the user. The lack of straps and additional attachment means provides a more comfortable sleep for the user due to the elimination of the straps as well as the minimization of the unit altogether.

A mild adhesive may be applied to the underside of the bendable element 316 to hold it in place against the user's face. Such adhesive must be mild enough that the element can be easily removed by the user without causing significant discomfort or irritation or abrasion. The adhesive may also be a soft foam or non-foam (such as a silicone) adhesive. Further, the adhesive may include a slit so that it can slide onto the bendable element 316.

In the embodiment illustrated in FIGS. 9-12, the adhesive 346 is positioned along the underside of the bendable element 316 to adhere to the user's skin, primarily along the first bend 326 of the bendable element 316. Second and third adhesives 348, 350 may optionally be positioned along the bendable element 316 between the second and third bends 328, 330 and the fourth and fifth bends 332, 334, respectively. In the illustrated embodiment, an inner surface 316a of the bendable element 316 includes first and second grooves 316b, 316c that receive the adhesive 346 as shown in FIG. 11A. Each groove 316b, 316c is formed by first and second ledges 316d, 316e extending from first and second outer edges 316f, 316g of the bendable element 316. The adhesive 346 includes an outer adhesive surface 346a spaced apart from an inner non-adhesive surface 346b by a body 346c. The inner surface 346b is positioned within the first and second grooves 316b, 316c, and the outer surface 346a is positioned outwardly of the grooves 316b, 316c. The sizes, shapes, and dimensions of the grooves 316b, 316c of the bendable element 316 and surfaces 346a, 346c and body 346b of the adhesive 346 may vary from those shown in the illustrated embodiment of FIG. 11A as desired or necessary. The grooves 316b, 316c may be formed along the length of the bendable element 316 or at discrete portions of the bendable element 316.

In an alternative embodiment, a single adhesive may be applied that extends between the first and second side portions 336, 338, optionally including the second and third bends, 328, 330, across the first bend 326. Examples of suitable adhesives include Scotch® Restickable Tabs (1"× 1") or Dots (⅞"×⅞"). The adhesives 346, 348, 350 may be reused a number of times (rewetting with water as necessary), and easily replaced as necessary. Another suitable adhesive is a polyolefin foam tape for dermatological use, such as 3M® CoTran™ 9773 Tape. In other embodiments, any number of adhesives may be used as necessary to sufficiently secure the bendable element 316 to the user's face. In an alternative embodiment, first and second edges of the adhesive 346 may be pre-coiled so that they can be easily received by the first and second grooves 316b, 316c of the bendable element 316. The adhesive stability improves as the bendable element 316 is bent because such bending improves the retention of the adhesive 346 within the grooves 316b, 316c. In another embodiment shown in FIG. 13B, the adhesive 346d has a tubular shape that is threaded onto the bendable element 316. The outer surface of the adhesive 346d may be completely adhesive or may include adhesive and non-adhesive portions. For example, the tubular adhesive 346d may include an inner adhesive portion along the inner surface of the bendable element and an outer non-adhesive portion along the outer surface of the bendable element.

Figure 13A:
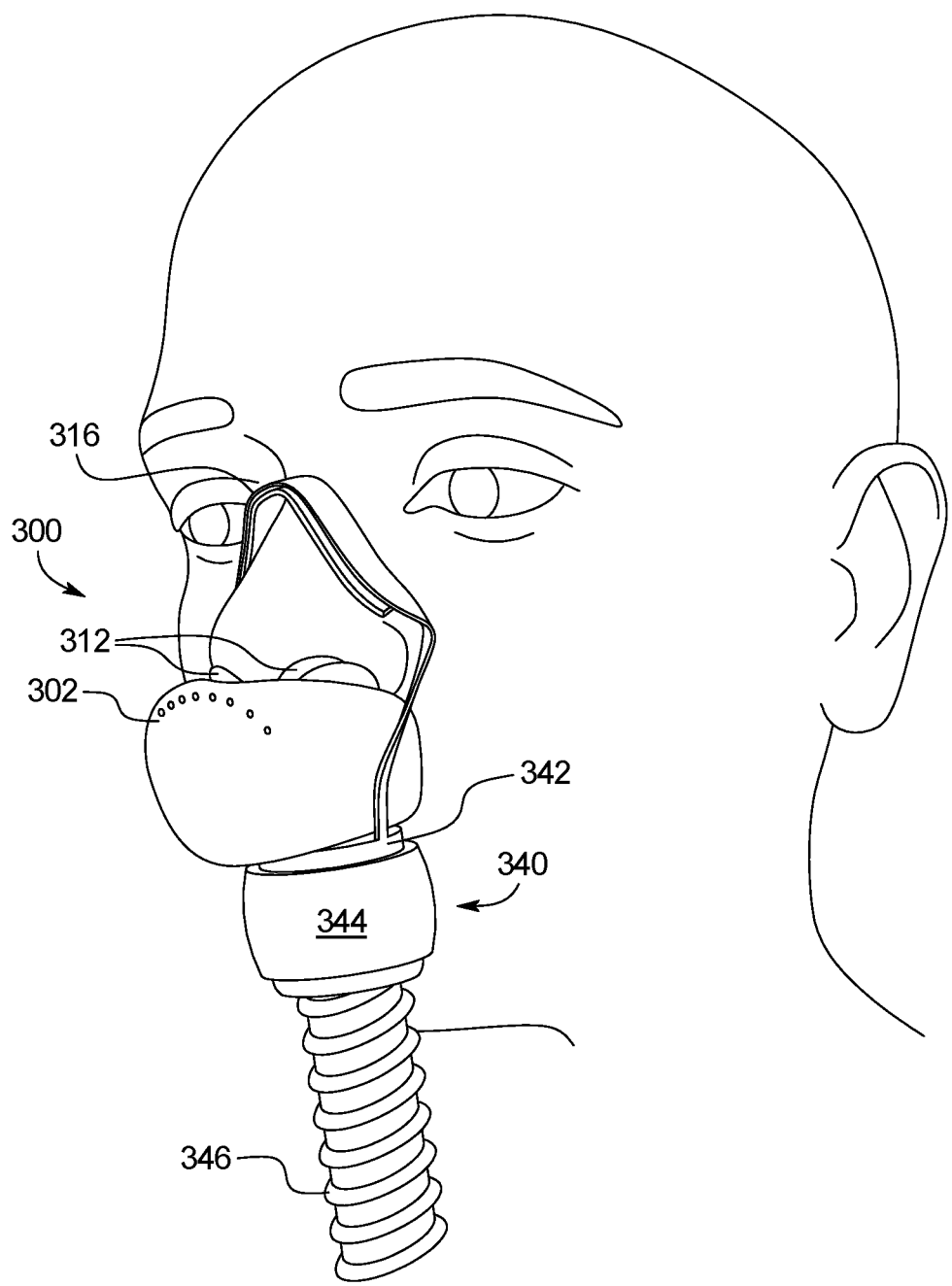
FIG. 13A is a perspective view of an alternative air supply interface for use with any of the illustrated embodiments.
Figure 13B:
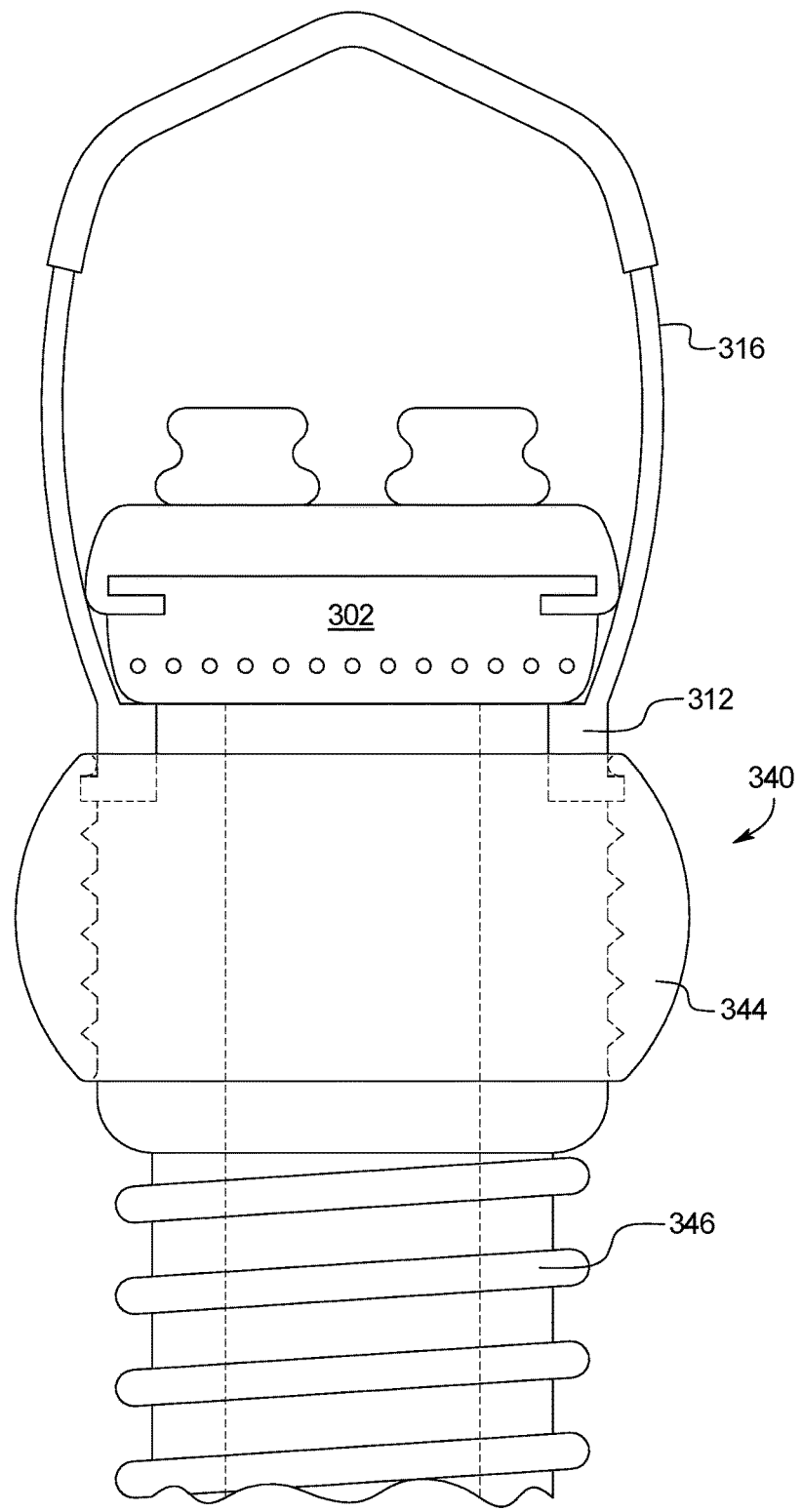
FIG. 13B is a front elevational view of the alternative air supply interface of FIG. 13A.

In a further embodiment illustrated in FIGS. 13A and 13B, the air supply interface 302 includes an adjusting device 340 to modify the height and position of the bendable element 316 relative to the air supply interface. The adjusting device includes a bendable element base 342 that is received by an adjustment dial 344. The adjustment dial is threaded onto a tubing connector 346. The first and second ends 318, 320 of the bendable element 316 are secured to or integral with the bendable element base 342 so that rotation of the adjustment dial 344 along the tubing connector 346 causes the first and second ends 318, 320 to move vertically, thereby causing the bendable element 316 to adjust for varying sizes and heights of users' noses.

Figure 14A:
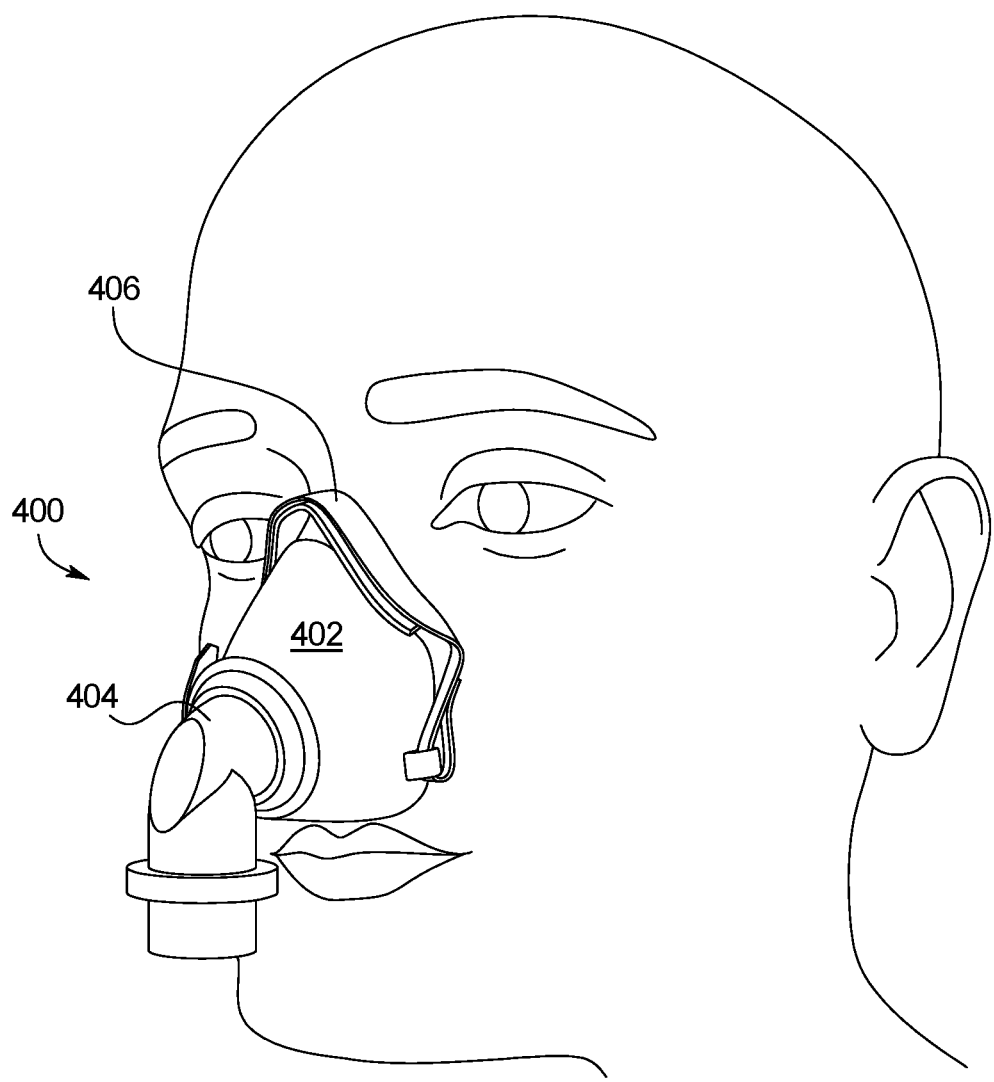
FIG. 14A is a further embodiment of the nasal interface device of the present application including a nose mask.
Figure 14B:
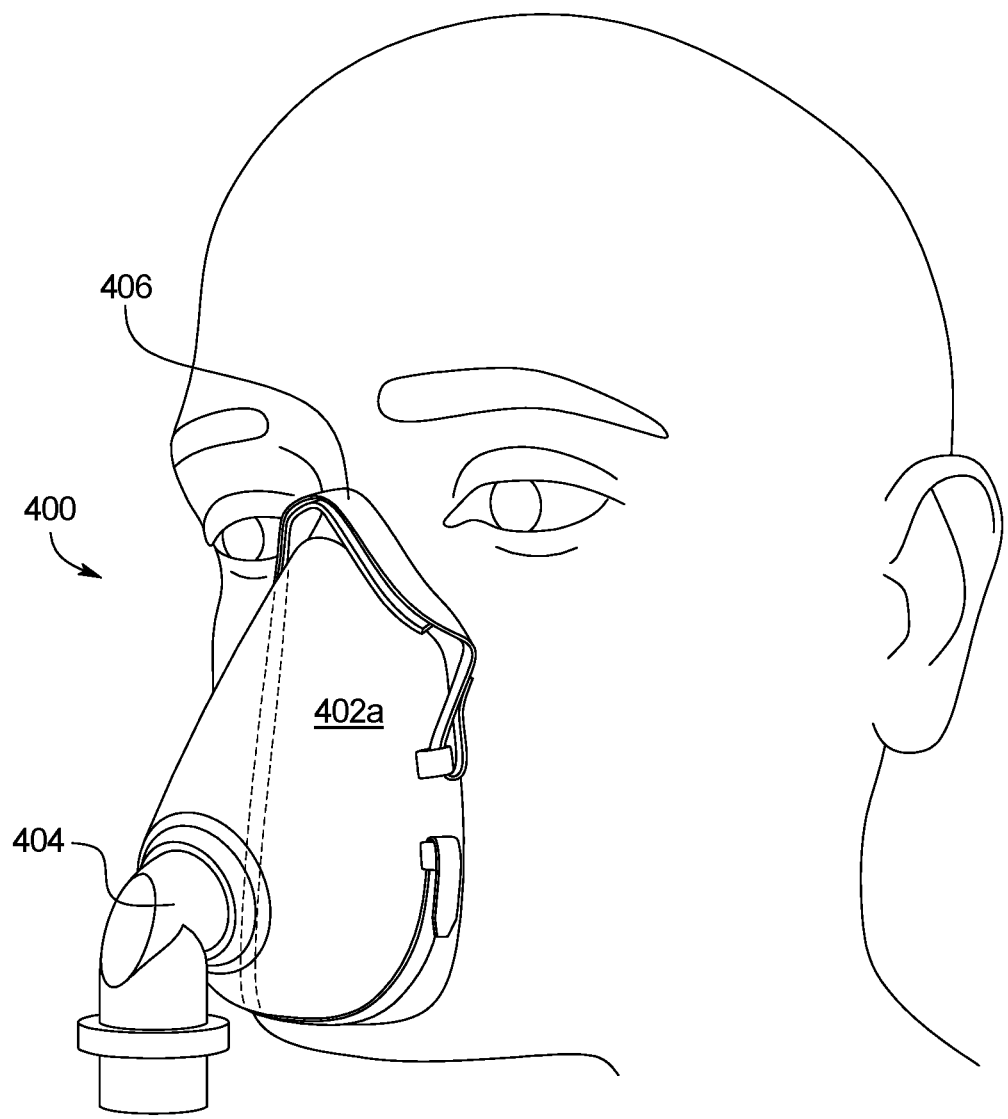
FIGS. 14B and 14C are further embodiments of the nasal interface device of the present application including a nose and mouth mask.
Figure 14C:
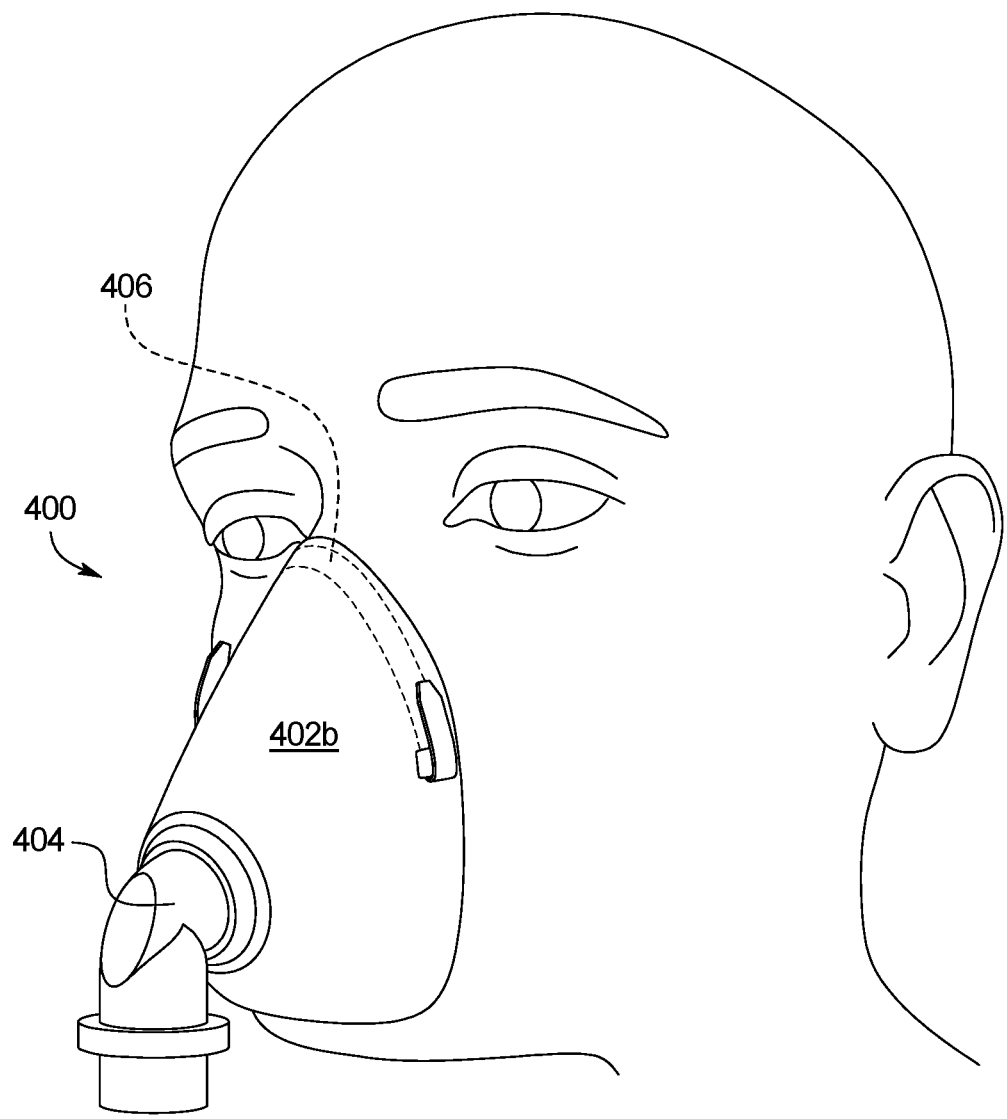

FIGS. 14A-14C illustrate further embodiments of the strapless nasal interface device 400 that is similar to the strapless nasal interface device 300 except for the features described as follows. The primary difference is the use of a nose mask 402 in lieu of the nostril interface tubes 312. As shown in FIGS. 14A-14C, the nose mask 402 is connected to an air supply interface 404. In FIG. 14A, the nose mask 402 covers the nose of the user. In FIGS. 14B and 14C, each of the nose masks 402a and 402b covers the mouth in addition to the nose. In FIGS. 14A and 14B, the bendable element 406, 406b is positioned outside of the nose mask 402, 402a, while in FIG. 14C, the bendable element 406c is positioned along the underside of the nose mask 402 at an outer edge 408. Each of the nose masks 402, 402a of FIGS. 14A and 14B include a handle 408, 408a through which an end of the bendable element 406, 406a is threaded and wrapped around in order to secure the positioning of the bendable element 406, 406a relative to the nose mask 402, 402a. The bendable element 406b shown in FIG. 14B extends along the bottom of the nose mask 402a and is threaded through a second handle 410a to secure positioning as well. Other manners of securing the bendable element to the nose mask are envisioned.

The nose mask 402 is shaped in such a manner to form a seal or snug fit with the face of the user. Air flows from a body 410 of the air supply interface 404 into the nose mask 402 and is inhaled by the user. Similar to the bendable element 316 of the nasal interface device 300, the bendable element 406 is a metallic strip that corresponds to contours of the user's nose and face. The plasticity of the material of the bendable element 406 is deformable so that it bends to match contours of the user's nose while maintaining its shape so as to secure the positioning of the air supply interface 404 relative to the user's nose. The height of the bendable element 406 may be adjusted for various sizes and shapes of users' noses.

Figure 15:
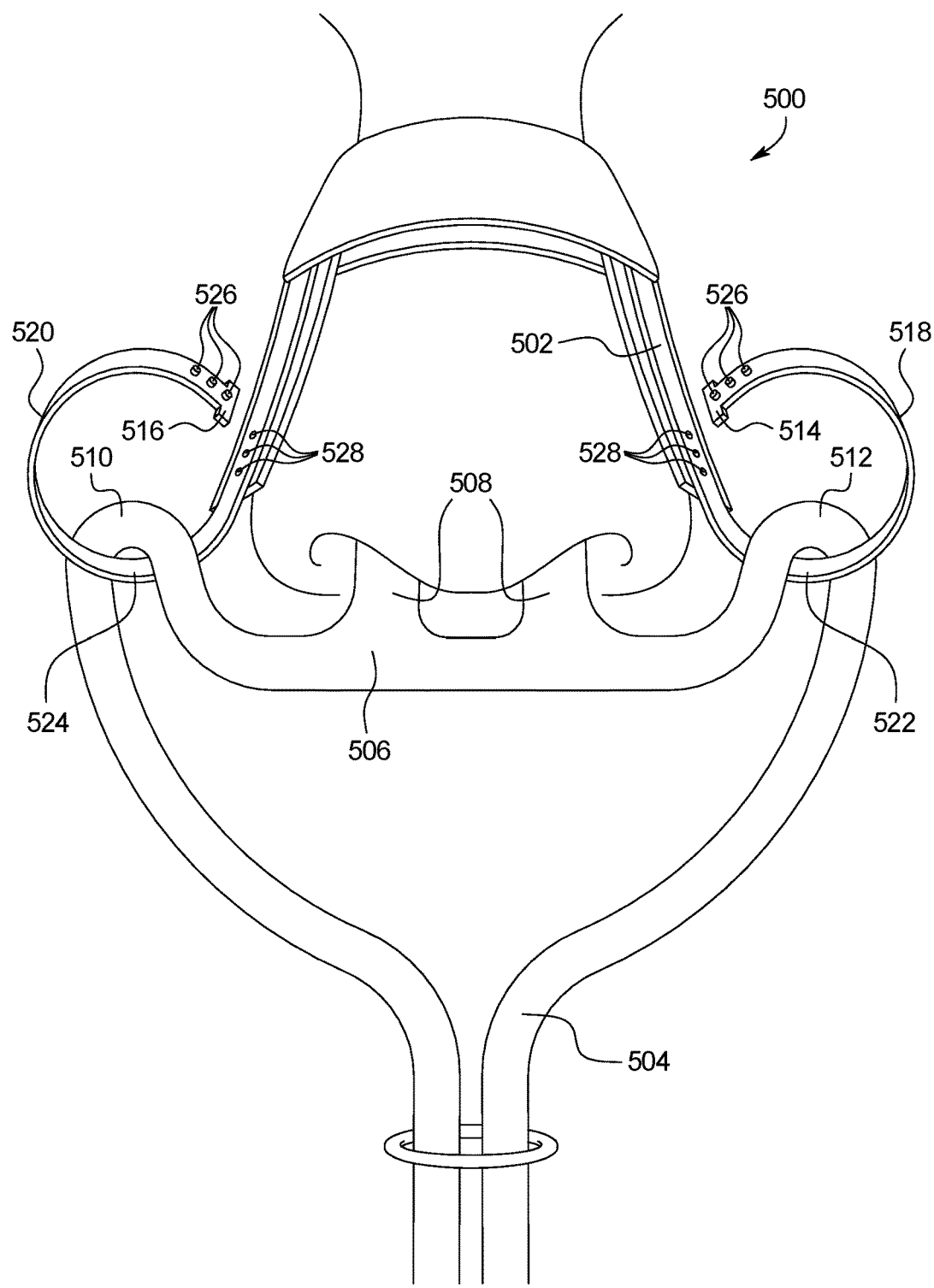
FIG. 15 is a further embodiment of the nasal interface device of the present application adapted for use with a cannula.

Referring to FIG. 15, a further embodiment of the strapless nasal interface device 500 includes a bendable element 502 that engages with an air supply interface 504. In this embodiment, the air supply interface 504 is a cannula 506 including a pair of nasal prongs 508 and first and second lanyards 510, 512 extending from either side of the nasal prongs 508.

Similar to the bendable elements 316, 406 of the nasal interface devices 300, 400, respectively, of FIGS. 9 and 14, respectively, the bendable element 502 is a metallic strip that corresponds to contours of the user's nose and face. The plasticity of the material of the bendable element 502 is deformable so that it bends to match contours of the user's nose while maintaining its shape so as to secure the positioning of the cannula relative to the user's nose.

The bendable element 502 includes first and second ends 514, 516 and first and second bends 518, 520 adjacent the bridge area of the user's nose during use. The curvature of the bendable element 502 near the first and second ends 514, 516 provides first and second platforms or shelves 522, 524, respectively, that engage the first and second lanyards 510, 512 of the cannula 506. In other embodiments, the bendable element 502 may be free of bends or may include any number of bends as desired to facilitate corresponding to contours of the user's nose.

Figure 16:
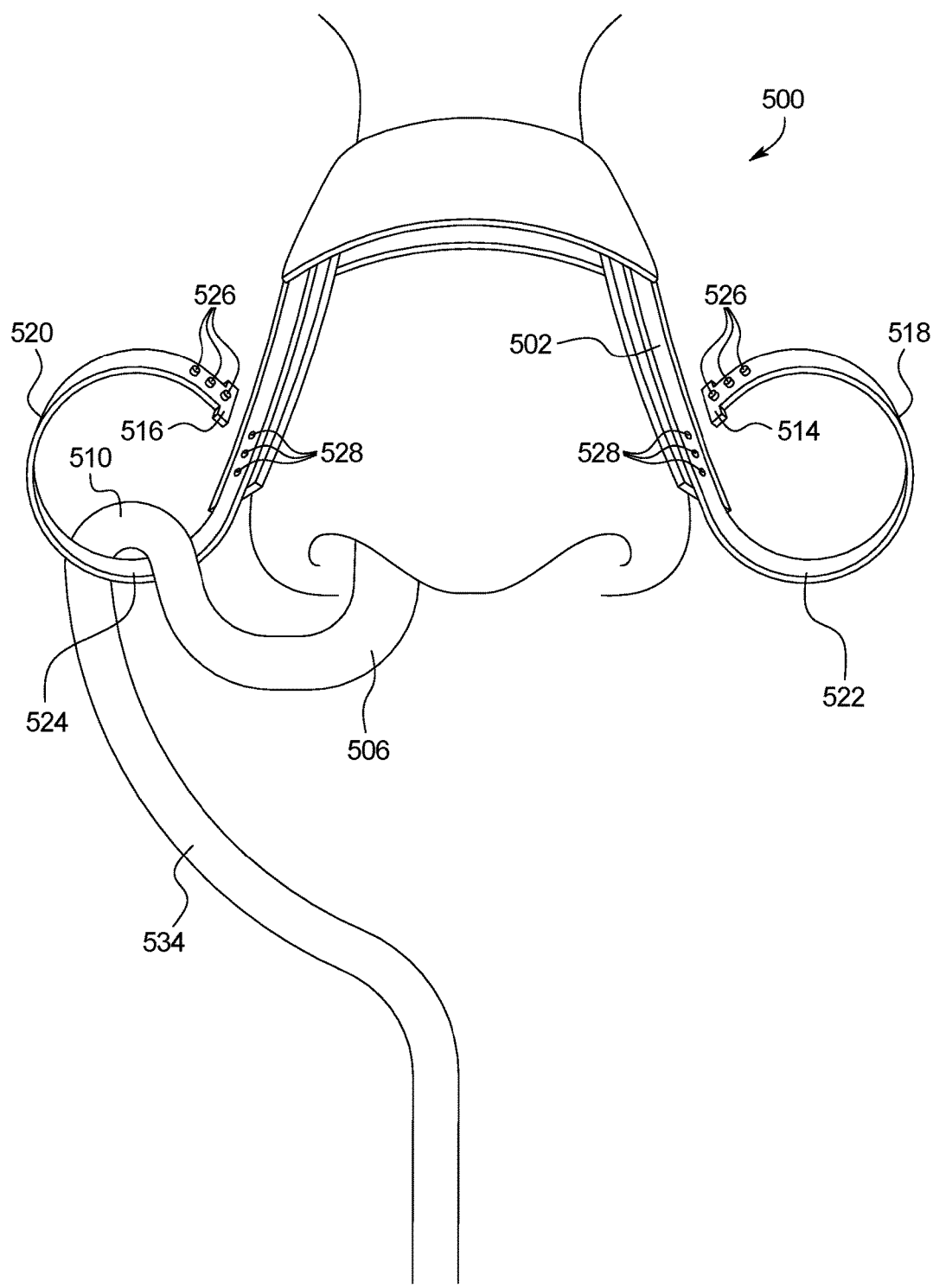
FIG. 16 is a further embodiment of the nasal interface device of the present application for use with a feeding tube.

Referring to FIG. 15, the first and second lanyards 510, 512 are positioned on the first and second platforms 522, 524 of the bendable element 502 to assist in positioning the nasal prongs 508 of the cannula 506 adjacent to or within the user's nostrils. As shown in FIG. 16, the nasal interface device 500 may be used to maintain the position of a feeding tube 534 relative to the user's nostrils. Specifically, the first and second platforms 522, 524 of the bendable element 502 support and maintain the position of the feeding tube 534 adjacent to or within the user's nostrils.

In the embodiment illustrated in FIG. 15, protrusions 526 extending from the first and second ends 514, 516 engage with openings 528 along first and second side portions 530, 532 of the bendable element 502 so that the user can adjust the sizing and shape of the platforms 522, 524. The device 500 may include other suitable fasteners such as, but not limited to, buttons and/or clasps for securing the first and second ends to first and second side portions of the bendable element.

Figure 17:
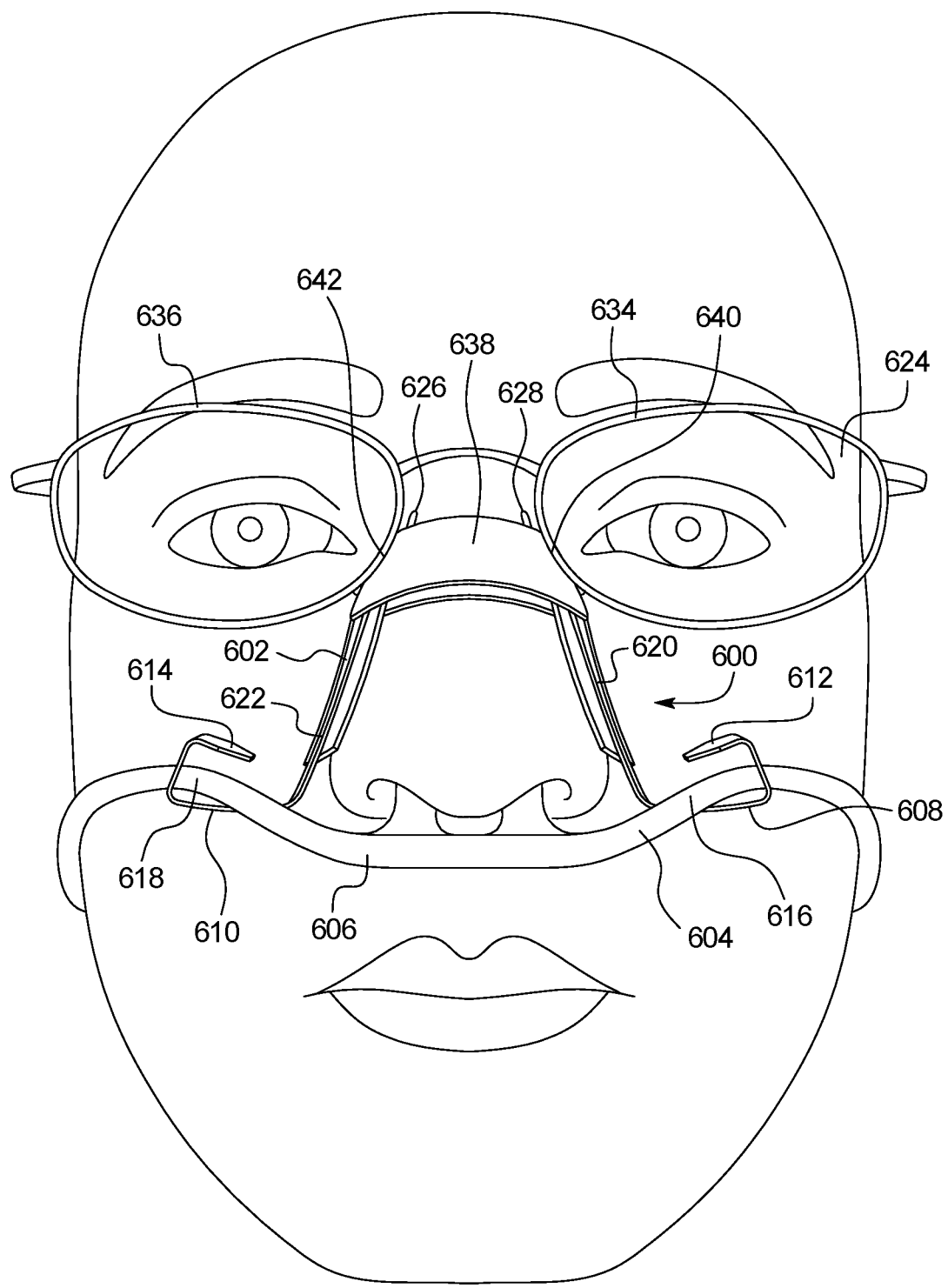
FIG. 17 is a further embodiment of the nasal interface device of the present application adapted for use with a cannula.

FIG. 17 illustrates an embodiment of the strapless nasal interface device 600 that is similar to the device 500 of FIG. 15 in that it includes a bendable element 602 that engages with an air supply interface 604 comprising a cannula 606. The bendable element 602 is shaped to form first and second platforms 608, 610 adjacent first and second ends 612, 614, respectively, for supporting first and second lanyards 616, 618 of the cannula 606. In the illustrated embodiment, the first and second ends 612, 614 remain free from first and second side portions 620, 622 of the bendable element 602.

The strapless nasal interface device 600 may be secured to a pair of glasses 624 that has first and second pad arms 626, 628 that carry first and second nose pads (not shown), respectively, adjacent first and second frames 634, 636, respectively. Specifically, the bendable element 602 includes a bridge portion 638 between the first and second side portions 620, 622. First and second ends 640, 642 of the bridge portion 638 may be held between the first and second pad arms 626, 628, respectively, and the first and second frames 634, 636, respectively.

While the above describes example embodiments of the present disclosure, these descriptions should not be viewed in a limiting sense. Rather, several variations and modifications can be made without departing from the scope of the present disclosure.

What is claimed is:

1. A nasal interface device configured to be positioned about a nasal bone of a bridge, a first side, and a second side of a user's nose, comprising:
   an air supply interface body including an air supply opening, at least one nasal opening, and first and second attachment surfaces;
   a bendable metallic member including a bridge portion between first and second ends, wherein the bridge portion compresses downward over the nasal bone of the bridge of the user's nose and the bendable metallic member compresses downward toward the first and second sides of the user's nose;
   an adhesive secured to an underside of the bendable metallic member;
   a first elastic member having a first proximal end and a first portion, the first proximal end including a first coupling means for directly or indirectly attaching to the first end of the bendable metallic element, and the first portion engaging with the first attachment surface on the air supply interface body; and
   a second elastic member having a second proximal end and a second portion, the second proximal end including a second coupling means for directly or indirectly attaching to the second end of the bendable metallic element, and the second portion engaging with the second attachment surface on the air supply interface body;
   wherein each of the first and second elastic members has a Young's modulus of between about 0.01 and about 0.1 GPa;
   wherein each of the first and second elastic members are separate and apart from each other and the air supply interface body, and wherein the first and second portions of the first and second elastic members are adjustable in position on the air supply interface body; and
   wherein each of the first and second elastic members is pulled taut in order to form a seal where the air supply interface body meets the user's nose without needing straps extending around the user's head and neck.

2. The nasal interface device of claim 1, wherein each of the first and second elastic members has a length of between about 5 cm and about 6 cm.

3. The nasal interface device of claim 1, wherein each of the first and second elastic members comprises a rubber material.

4. The nasal interface device of claim 1, wherein each of the first and second elastic members comprises a woven elastic band.

5. The nasal interface device of claim 1, further comprising first and second rings connected to the first and second ends of the bendable metallic member, respectively, wherein the first and second elastic members extend through the first and second rings, respectively.

6. The nasal interface device of claim 5, wherein the first and second coupling means comprise a hook and loop material, and wherein each of the first and second elastic members including a corresponding hook and loop material to receive the first and second coupling means of the first and second elastic members, respectively.

7. The nasal interface device of claim 5, wherein each of the first and second coupling means has a length of at least about 3 cm.

8. The nasal interface device of claim 1, wherein each of the first and second elastic members extends from the first and second ends, respectively, of the bendable metallic member and through the first and second attachment surfaces, respectively.

9. The nasal interface device of claim 8, wherein each of the first and second coupling means comprise an adhesive tape configured to adhere to the user's nose.

10. The nasal interface device of claim 1, wherein each of the first and second coupling means comprise an adhesive tape configured to adhere to the user's nose.

11. The nasal interface device of claim 10, wherein each of the first and second coupling means has a length of about 3 cm.

12. The nasal interface device of claim 1, wherein the air supply interface connects to one of a ventilator, a continuous positive airway pressure (CPAP) machine, and a bilevel positive airway pressure (BiPAP) machine.

13. A method of wearing a nasal interface device about a nasal bone of a bridge, a first side, and a second side of a user's nose, comprising the steps of:
providing the nasal interface device comprising:
an air supply interface body including an air supply opening, at least one nasal opening, and first and second attachment surfaces;
a bendable metallic member including a bridge portion between first and second ends;
an adhesive secured to an underside of the bendable metallic member;
a first elastic member having a first proximal end and a first portion, the first proximal end including a first coupling means for directly or indirectly attaching to the first end of the bendable metallic element, and the first portion engaging with the first attachment surface on the air supply interface body; and
a second elastic member having a second proximal end and a second portion, the second proximal end including a second coupling means for directly or indirectly attaching to the second end of the bendable metallic element, and the second portion engaging with the second attachment surface on the air supply interface body;
wherein each of the first and second elastic members has a Young's modulus of between about 0.01 and about 0.1 GPa;
wherein each of the first and second elastic members are separate and apart from each other and the air supply interface body, and wherein the first and second portions of the first and second elastic members are adjustable in position on the air interface body;
compressing the bridge portion of the bendable metallic element downward over the nasal bone of the bridge and toward the first and second sides of the user's nose;
positioning the air supply interface body about the user's nose, wherein the first and second attachment surfaces of the air supply interface body are adjacent to the first and second sides, respectively, of the user's nose;
adjusting the first and second portions of the first and second elastic members on the air interface body;
pulling the first and second elastic members taut in order to form a seal where the air supply interface body meets the user's nose; and
securing each of the first and second coupling means to maintain the seal without needing straps extending around the user's head and neck.

14. The method of claim 13, wherein the first and second coupling means comprise a hook and loop material, and wherein each of the first and second elastic members including a corresponding hook and loop material to receive the first and second coupling means of the first and second elastic members, respectively.

15. The method of claim 13, further comprising the steps of:
extending the first elastic member across the user's nose to position the first coupling means on the second side of the user's nose; and
extending the second elastic member across the user's nose to position the second coupling means on the first side of the user's nose.

16. The method of claim 13, further comprising the steps of:
extending the first coupling means across the bridge of the user's nose; and
extending the second coupling means across the bridge of the user's nose.

17. The nasal interface device of claim 1, wherein the first portion of the first elastic member comprises a first distal end opposite the first proximal end, and wherein the second portion of the second elastic member comprises a second distal end opposite the second proximal end.

18. The method of claim 13, wherein the first portion of the first elastic member of the nasal interface device comprises a first distal end opposite the first proximal end, and wherein the second portion of the second elastic member of the nasal interface device comprises a second distal end opposite the second proximal end.

* * * * *